(12) United States Patent
Weissman et al.

(10) Patent No.: US 11,766,454 B2
(45) Date of Patent: Sep. 26, 2023

(54) USE OF TLR AGONIST AND ANTI-CD47 AGENT TO ENHANCE PHAGOCYTOSIS OF CANCER CELLS

(71) Applicant: The Board of Trustees of the Leland Stanford Junior University, Stanford, CA (US)

(72) Inventors: Irving L. Weissman, Stanford, CA (US); Mingye Feng, Mountain View, CA (US); Jens-Peter Volkmer, Menlo Park, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 175 days.

(21) Appl. No.: 16/997,738

(22) Filed: Aug. 19, 2020

(65) Prior Publication Data
US 2021/0038643 A1     Feb. 11, 2021

Related U.S. Application Data

(63) Continuation of application No. 15/543,095, filed as application No. PCT/US2016/014334 on Jan. 21, 2016, now Pat. No. 10,780,117.
(Continued)

(51) Int. Cl.
*A61K 39/395*     (2006.01)
*A61K 35/15*      (2015.01)
(Continued)

(52) U.S. Cl.
CPC .......... *A61K 35/15* (2013.01); *A61K 31/4745* (2013.01); *A61K 31/519* (2013.01);
(Continued)

(58) Field of Classification Search
None
See application file for complete search history.

(56) References Cited

U.S. PATENT DOCUMENTS 9,045,541 B2 *  6/2015  Eckelman ........ C07K 14/70503
9,623,079 B2 *  4/2017  Willingham ....... A61K 39/3955
(Continued)

FOREIGN PATENT DOCUMENTS

| WO | WO2011/136828 | 11/2011 |
|----|---------------|---------|
| WO | WO 2014/149477 | 9/2014 |
| WO | WO2016118754 | 7/2016 |

OTHER PUBLICATIONS

Hennessy et al., Targeting Toll-like receptors: emerging therapeutics?, Nat. Rev. Drug Disc. 9:293-307, 2010.*
(Continued)

*Primary Examiner* — Claire Kaufman
(74) *Attorney, Agent, or Firm* — Pamela J. Sherwood; Bozicevic, Field & Francis LLP

(57) ABSTRACT

Therapeutic and diagnostic methods are provided, which methods relate to the induction of expression of calreticulin on phagocytic cells. Specifically, the methods relate to macrophage-mediated programmed cell removal (PrCR), the methods comprising increasing PrCR by contacting a phagocytic cell with a toll-like receptor (TLR) agonist; or down-regulating PrCR by contacting a phagocytic cell with an inhibitor of Bruton's tyrosine kinase (BTK). In some embodiments, an activator of TLR signaling or a BTK agonist is provided in combination with CD4 7 blockade.

10 Claims, 13 Drawing Sheets

Specification includes a Sequence Listing.

FIG. 7C

Related U.S. Application Data

(60) Provisional application No. 62/106,050, filed on Jan. 21, 2015.

(51) Int. Cl.

| | | |
|---|---|---|
| *A61K 31/4745* | (2006.01) | |
| *A61K 31/713* | (2006.01) | |
| *A61K 39/39* | (2006.01) | |
| *C07K 16/28* | (2006.01) | |
| *A61K 31/519* | (2006.01) | |
| *A61K 45/06* | (2006.01) | |
| *C12N 5/0786* | (2010.01) | |
| *A61K 39/00* | (2006.01) | |

(52) U.S. Cl.
CPC ............ *A61K 31/713* (2013.01); *A61K 39/39* (2013.01); *A61K 39/3955* (2013.01); *A61K 45/06* (2013.01); *C07K 16/2896* (2013.01); *C12N 5/0645* (2013.01); *A61K 2039/55511* (2013.01); *A61K 2039/55583* (2013.01); *C12N 2501/50* (2013.01); *C12N 2501/599* (2013.01)

(56) References Cited

U.S. PATENT DOCUMENTS

| | | |
|---|---|---|
| 2011/0070269 A1 | 3/2011 | Wood et al. |
| 2013/0309244 A1 | 11/2013 | Tedder et al. |
| 2013/0336922 A1 | 12/2013 | Weinschenk et al. |
| 2014/0271683 A1 | 9/2014 | Chao et al. |
| 2016/0058793 A1 | 3/2016 | Terman et al. |

OTHER PUBLICATIONS

National Center for Biotechnology Information, PubChem Compound Summary for CID 57469, Imiquimod. [retrieved on Jul. 1, 2022] Retrieved online from<URL:https://pubchem.ncbi.nlm.nih.gov/compound/Imiquimod>, 2022.*
Feng et al., Programmed cell removal by clareticulin in tissue homeostasis and cancer, Nat. Commun. 9:3194 (2018), 15 pages, doi.org/10.1038/s41467-018-05211-7.*
Byrne et al., "Bruton Tyrosine Kinase Is Required for Apoptotic Cell Uptake via Regulating the Phosphorylation and Localization of Calreticulin", Journal of Immunology, Apr. 17, 2013, pp. 5207-5215, vol. 190, No. 10, The American Association of Immunologists, Inc., Rockville, MD.
Chao et al. (2010) alreticulin is the dominant pro-phagocytic signal on multiple human cancers and is conuterbalanced by CD47, Sci. U Translational Med. 2(63):1-9.
Chao et al., "The CD47-SIRPα pathway in cancer immune evasion and potential therapeutic implications", Current Opinion in Immunology, Apr. 1, 2012, pp. 225-232, vol. 24. No. 2, Elsevier, New York City, NY.
Cyrus, (2018) "The role of tumor-associated macrophages in human skin cancer", Yale University, EliScholar, abstract, pp. 11-13 and 25.
Feng et al., (2015) "Macrophages eat cancer cells using their own cal reticulin as a guide: Roles of TLR and Btk", Proc Natl Acad Sci US A, pp. 2145-2150, vol. 112(7), PNAS, Washington, DC.
Kreig et al. (2007) Development of TLR agonists for cancer therapy, J. Clin. Invest. 117(5): 1184-1194.
Long et al., "Harnessing the antitumor potential of macrophages for cancer immunotherapy", Oncoimmunology, 2013, p. 1-9, vol. 2(12), Informa UK Limited, London, England.
Nilsson, A. (2009)Dept. Integrative Med. Biol. , Umea University, Sweden [<URL: Https://www.diva-ortal.org/samsh/get/diva2:278362/FULLTEXT01.pdf>].
Obeid et al. (2007) "Calreticulin exposure dictates the immunogenicity of cancer cell death", Nat. Med., 13(1):54-61.
Pankey et al., In vitro synergy of telavancin and rifampin against Enterococcus faecium resistant to both linexolid and vancomycin the Ochshner J. 13(1):61-65, 2013.
Rakoff-Nahoum et al. (2009) "Toll-like receptors and cancer" Nat. Rev. Canc. 9:57-63.
Sucher (2014) Searching for synergy in silica, in vitro and in vivo, Synergy, 1:30-43.
Tseng et al., "Anti-CD47 antibody-mediated phagocytosis of cancer by macrophages primes an effective antitumor T-cell response", Proc Natl Acad Sci US A, 2013, pp. 11103-11108, vol. 110(27), PNAS, Washington, DC.
Weiskopf et al.(2013) "Engineered SIRP Variants as Immunotherapeutic Adjuvants to Anticancer Antibodies", Science, pp. 88-91, vol. 341, No. 6141, American Association for the Advancement of Science, Washington, DC.
Zhang et al., (2016) Anti-CD47 treatment stimulates phagocytosis of glioblastoma by M1 and M2 polarized macrophages and promotes M1 polarized macrophages in vivo, PLOS ONE, 11 (4):e0153550.
Houot et al. (2011) "Targeting immune effector cells to promote antibody-induced cytotoxicity in cancer immunotherapy" Trends in Immunology, vol. 32, No. 11, pp. 510-516.
Cyrus (2013) The Role Of Tumor-Associated Macrophages In Human Skin Cancer, Yale University, pp. 1-66.

* cited by examiner

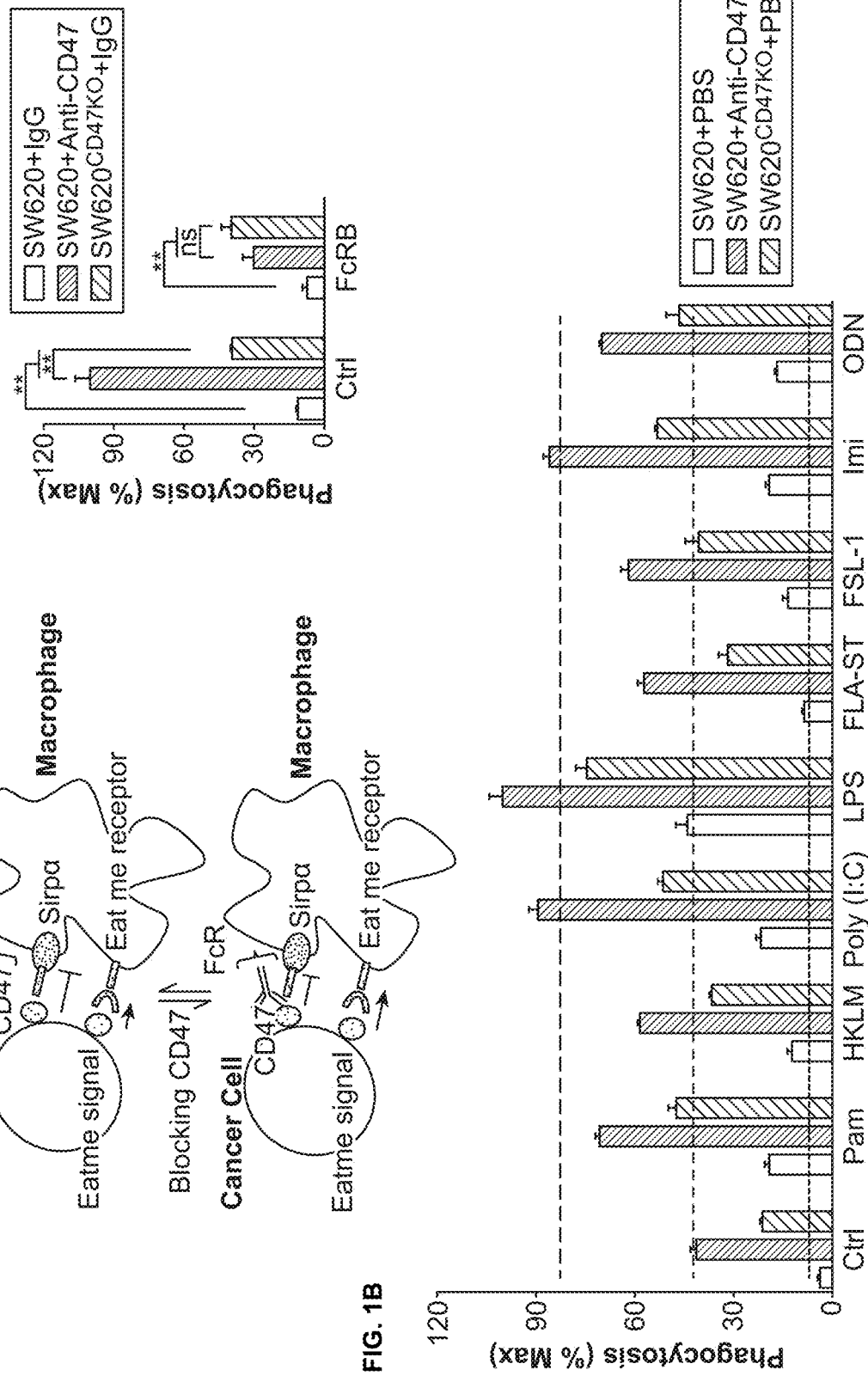

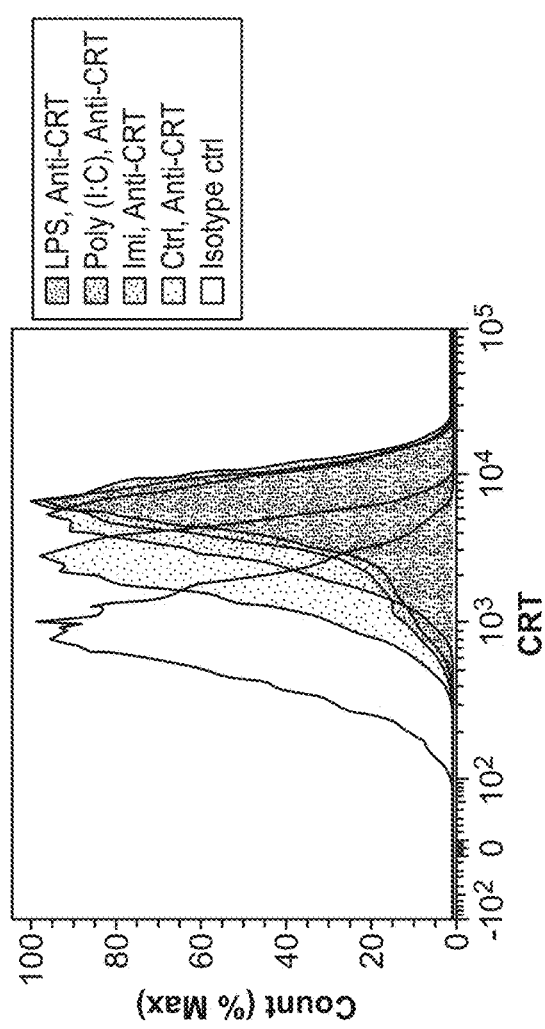
FIG. 3A
FIG. 3B
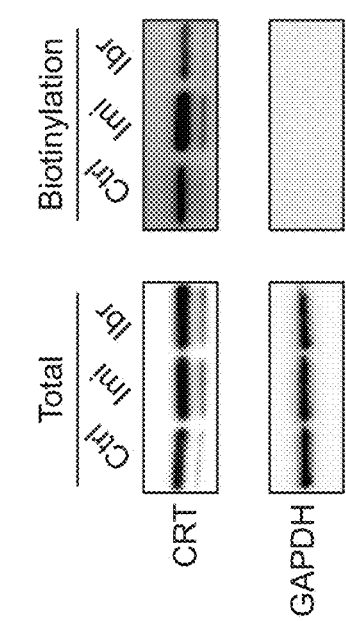
FIG. 3C
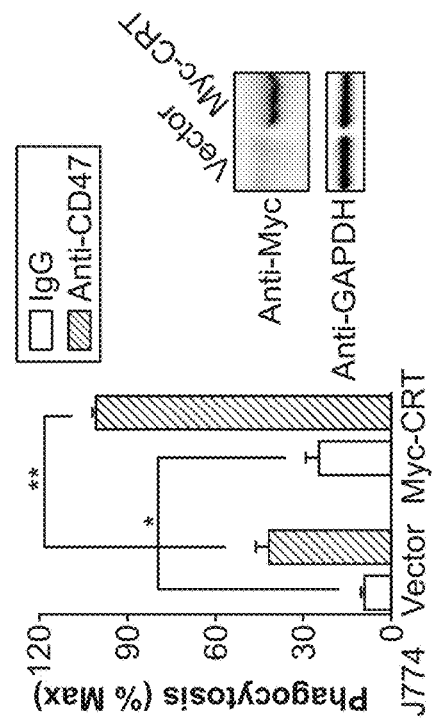
FIG. 3D

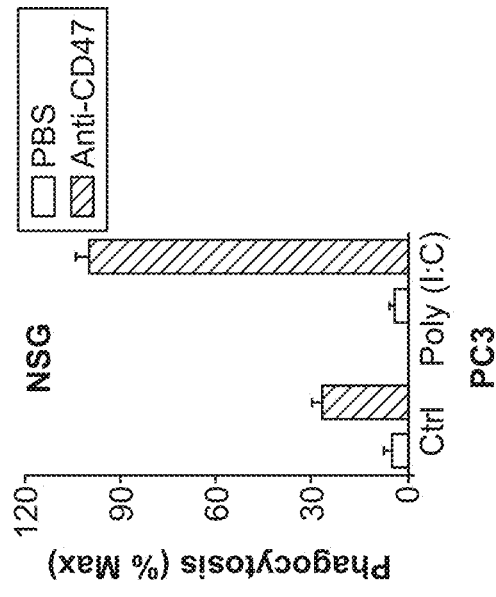
FIG. 7B
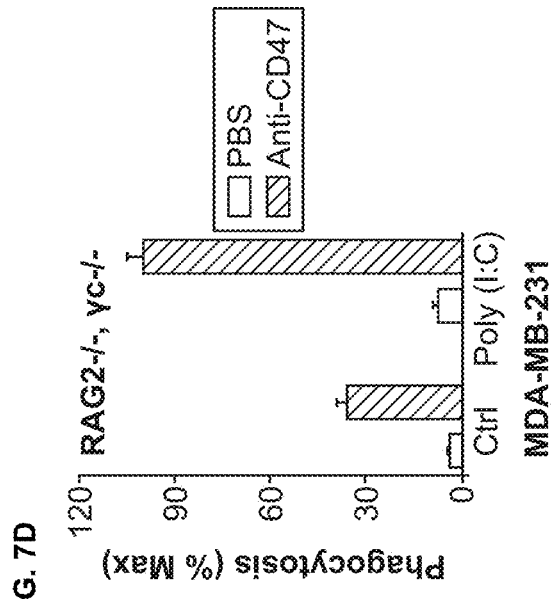
FIG. 7D
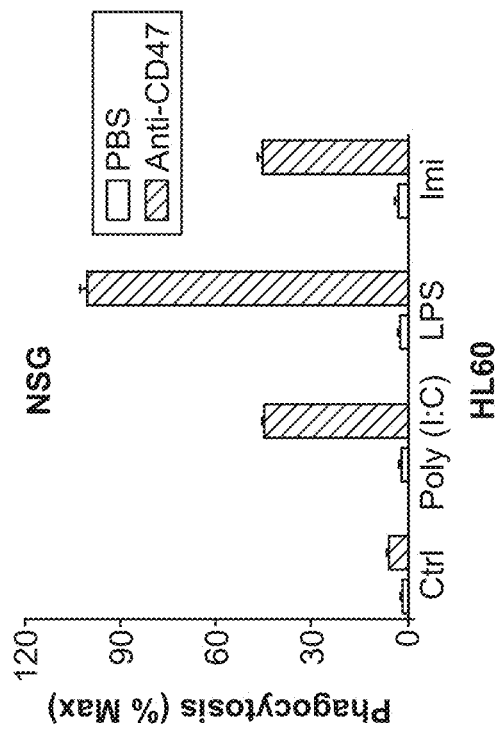
FIG. 7A
FIG. 7C

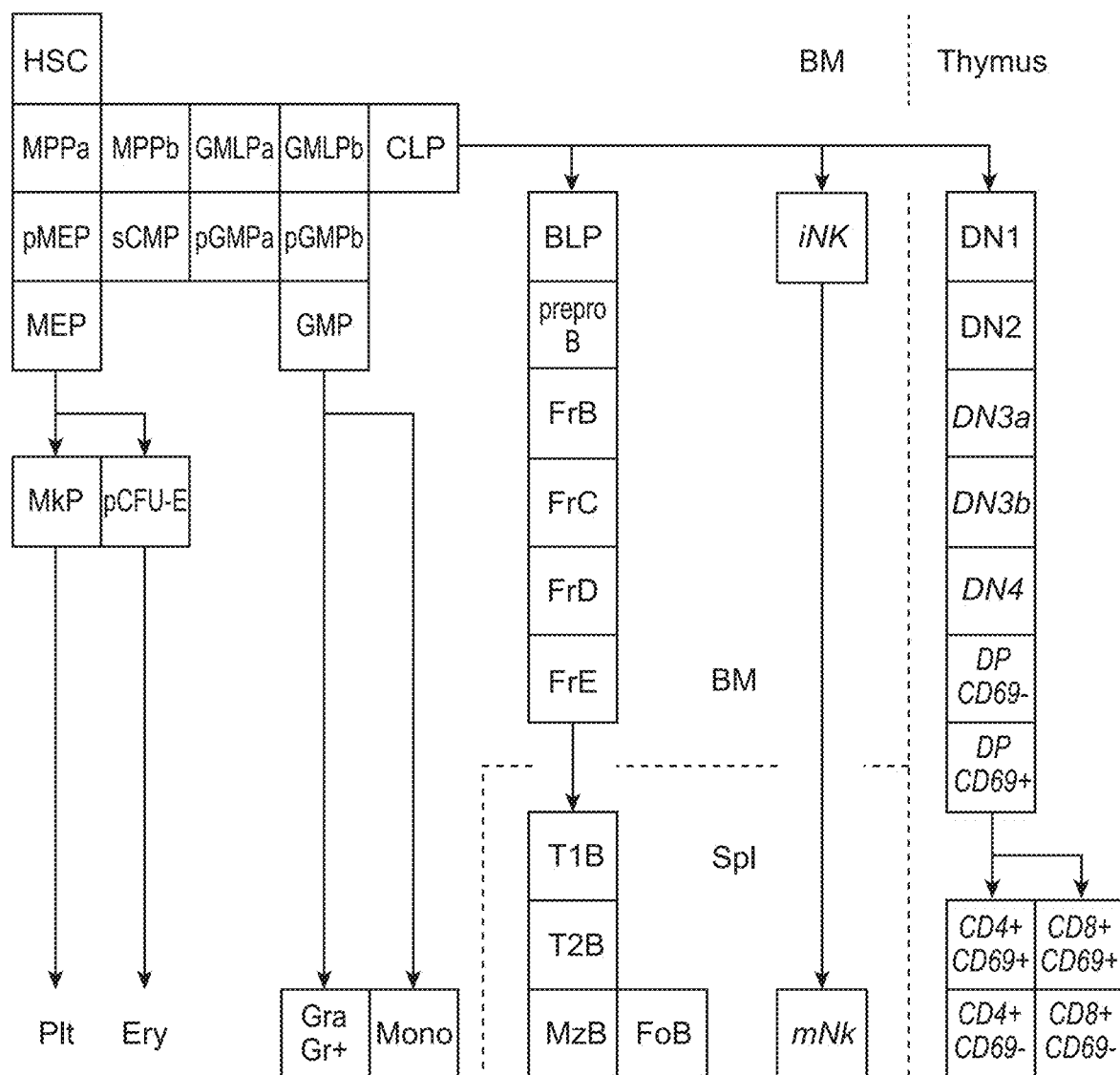
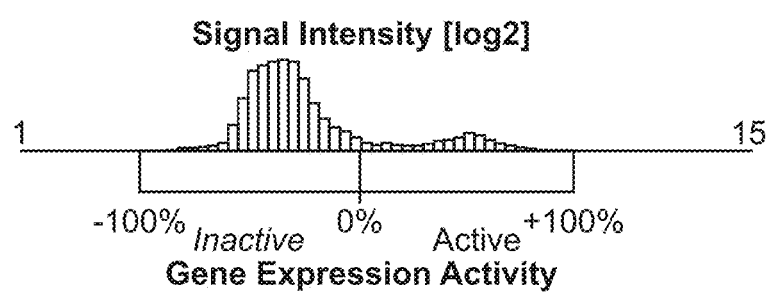
FIG. 9

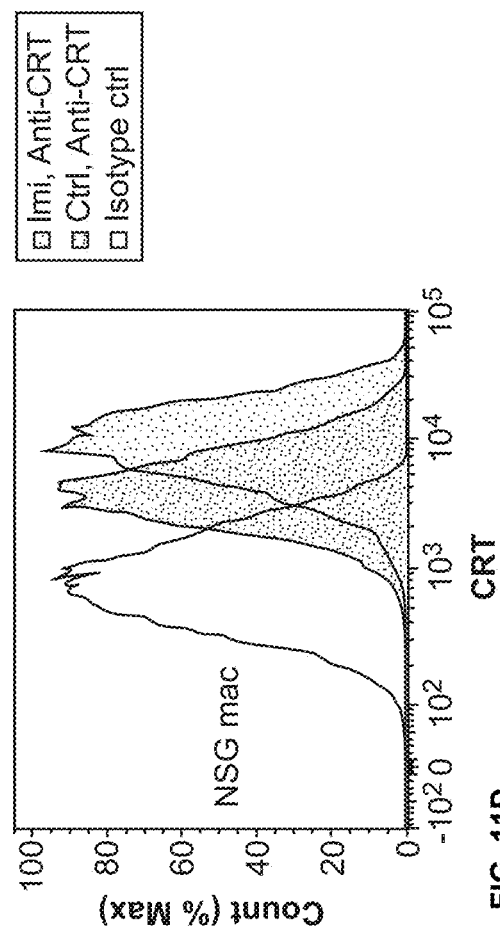
FIG. 11A
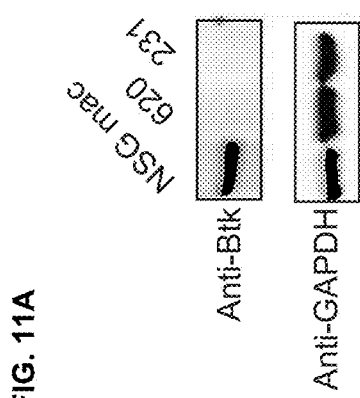
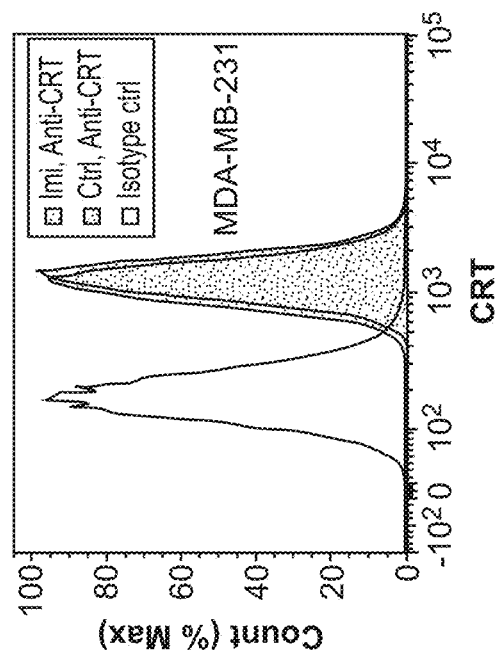
FIG. 11B
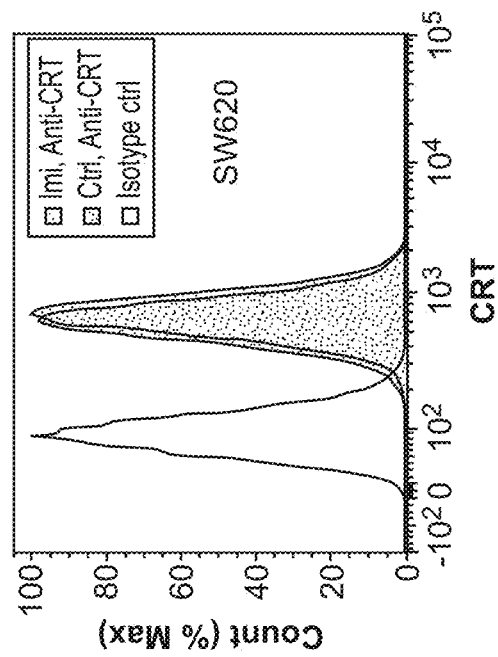
FIG. 11C
FIG. 11D

USE OF TLR AGONIST AND ANTI-CD47 AGENT TO ENHANCE PHAGOCYTOSIS OF CANCER CELLS

CROSS REFERENCE

This application is a continuation and claims the benefit of 371 application Ser. No. 15/543,095, filed Jul. 12, 2017, which claims the benefit of PCT Application No. PCT/US2016/014334, filed Jan. 21, 2016, which claims benefit of U.S. Provisional Patent Application No. 62/106,050, filed Jan. 21, 2015, which applications are incorporated herein by reference in their entirety.

BACKGROUND

The reticuloendothelial system (RES) is a part of the immune system. The RES consists of the phagocytic cells located in reticular connective tissue, primarily monocytes and macrophages. The RES consists of 1) circulating monocytes; 2) resident macrophages in the liver, spleen, lymph nodes, thymus, submucosal tissues of the respiratory and alimentary tracts, bone marrow, and connective tissues; and 3) macrophage-like cells including dendritic cells in lymph nodes, Langerhans cells in skin, and microglial cells in the central nervous system. These cells accumulate in lymph nodes and the spleen. The RES functions to clear pathogens, particulate matter in circulation, and aged or damaged hematopoietic cells.

To eliminate foreign cells or particles in the innate immune response, macrophage-mediated phagocytosis is induced when the phosphatidylserine receptor (PSR) reacts to phosphatidylserine (PS), which can be externalized from the membranes of dead cells, such as apoptotic and necrotic cells. In turn, the interaction between PS and PSR plays a crucial role in the clearance of apoptotic cells by macrophages. Once phagocytosis has been performed by macrophages, the inflammatory response is downregulated by an increase in factors such as IL-10, TGF-β, and prostaglandin E2 (PGE2). The strict balance between the inflammatory and anti-inflammatory responses in both innate and adaptive immunity plays a critical role in maintaining cellular homeostasis and protecting a host from extrinsic invasion.

The causal relationship between inflammation and the neoplastic progression is a concept widely accepted. Data now support the concept of cancer immunosurveillance—that one of the physiologic functions of the immune system is to recognize and destroy transformed cells. However, some tumor cells are capable of evading recognition and destruction by the immune system. Once tumor cells have escaped, the immune system may participate in their growth, for example by promoting the vascularization of tumors.

Both adaptive and innate immune cells participate in the surveillance and the elimination of tumor cells, but monocytes/macrophages may be the first line of defense in tumors, as they colonize rapidly and secrete cytokines that attract and activate dendritic cells (DC) and natural killer (NK) cells, which in turn can initiate the adaptive immune response against transformed cells.

Malignant cellular transformation occurs through a progression of genetic mutations and epigenetic reprogramming that activate oncogenes and inactivate tumor suppressor pathways leading to inheritance of several hallmarks shared by most cancer cells including: self-sufficiency in growth signals, insensitivity to anti-growth signals, tissue invasion and metastasis, poorly regulated replicative potential, sustained angiogenesis, and evasion of cell death by a variety of pathways, including apoptosis. In addition to these cell intrinsic properties, recent evidence suggests that many cancers are also able to evade the immune system through several distinct mechanisms.

Exploration of mechanisms by which cells avoid being cleared by phagocytosis can provide insight into ways for improving transplantation success of hematopoietic and progenitor stem cells, and improved methods of removing cancer cells from the body. The present invention satisfies these, and other, needs.

SUMMARY OF THE INVENTION

Therapeutic and diagnostic methods are provided, which methods relate to macrophage-mediated programmed cell removal (PrCR). It is shown herein that phagocytic cells, e.g. macrophages, in response to TLR signaling upregulate expression of calreticulin (CRT) on the phagocytic cell surface. The CRT on the surface of the phagocytic cell interacts with target cells, e.g. cancer cells, to initiate PrCR. The upregulation of CRT by the phagocytic cell is shown to involve a Bruton's tyrosine kinase (BTK) signaling pathway, and inhibition of BTK downregulates calreticulin on the phagocyte cell surface, thereby reducing PrCR. The methods of the invention increase PrCR by contacting a phagocytic cell with a TLR agonist; or down-regulate PrCR by contacting a phagocytic cell with an inhibitor of BTK. The contacting can be performed in vitro, e.g. to prime phagocytic cells for therapeutic purposes; or can be performed in vivo for therapeutic purposes. The expression of CRT on the phagocytic cell surface provides a biomarker for determining the phagocytic capability of the cell.

In one embodiments of the invention, an activator of TLR signaling or a BTK agonist is provided in combination with CD47 blockade, where the PrCr is increased relative to the cell removal in the presence of either agent as a monotherapy. In some embodiments, a population of cells comprising macrophages is contacted in vitro or in vivo with a dose of a TLR agonist or a BTK agonist that is effective in increasing CRT on the cell surface of the macrophage by at least about 25%, at least about 50%, at least about 75%, and may increase expression 2-fold, 3-fold, 5-fold or more, relative to an unstimulated cell. The level of phagocytosis in a cell thus treated may be at least about 25%, at least about 50%, at least about 75%, and may increase phagocytosis 2-fold, 3-fold, 5-fold or more, relative to an unstimulated cell. In the presence of an agent that blocks the interaction of CD47 with SIRPα, the incremental increase in phagocytosis for a cell treated with an effective dose of a TLR agonist or a BTK agonist may be at least about 25%, at least about 50%, at least about 75%, and may increase phagocytosis 2-fold, 3-fold, 5-fold or more, relative to a cell treated with a TLR agonist in the absence of CD47 blockade. In some embodiments the CD47 antagonist is an antibody. In some embodiments the antibody is hu5F9-G4.

For in vivo treatment, a TLR agonist or a BTK agonist may be administered in an effective dose and for a period of time sufficient to increase PrCr in the recipient, e.g. as determined by the phagocytosis of tumor cells by the phagocytic cells. The TLR agonist or a BTK agonist may be co-administered or concurrently administered with an effective dose of an agent that blocks the interaction of CD47 with SIRPα. The TLR agonist or a BTK agonist may be co-administered or concurrently administered with an agent that specifically targets a cancer cell, e.g. an antibody directed to a tumor selective target.

Phagocytic cells that have been treated in vitro with a TLR agonist or a BTK agonist can be administered to an individual for treatment of cancer, where the cells are administered systemically or locally, e.g. at a tumor site. The cells may be co-administered or concurrently administered with an effective dose of an agent that blocks the interaction of CD47 with SIRPα. The cells may be contacted with a tumor cell or tumor cell antigen in vitro prior to administration. The cells may be co-administered or concurrently administered with an agent that specifically targets a cancer cell, e.g. an antibody directed to a tumor selective target.

The phagocytic capability of a phagocyte, e.g. a macrophage, can be determined by measuring the expression of CRT on the cell surface, where an increase in CRT corresponds to an increase in phagocytic ability. In some embodiments, the expression of calreticulin on a macrophage cell surface is measured, including without limitation by contacting the cell with a CRT-specific antibody, and determining the quantity of antibody that is bound, e.g. by flow cytometry, ELISA, immunohistochemistry, and the like as known in the art. In some such embodiments the measuring step is performed after treating the cells with a TLR agonist in vitro. In some embodiments, the measuring is compared to a pre-determined level, or a control cell that is not treated with a TLR agonist. In some embodiments, cells that have a predetermined level of CRT are administered to an individual for treatment of cancer, where the cells are administered systemically or locally, e.g. at a tumor site.

In other embodiments of the invention, an inhibitor of BTK, including without limitation ibrutinib, anti-BTK antibody, etc., is provided in a therapeutic dose to an individual suffering from excessive or otherwise undesirable PrCR, including without limitation an individual suffering from a myelodysplastic syndrome (MDS), autoimmune hemolytic anemia, immune thrombocytopenic purpura (ITP), autoimmune diseases including rheumatoid arthritis, systemic lupus erythematosus, etc. The dose of BTK inhibitor is sufficient to downregulate expression of CRT on phagocytic cells, e.g. decrease by least about 25%, at least about 50%, at least about 75%, and may decrease expression 2-fold, 3-fold, 5-fold or more, relative to an unstimulated cell. The level of phagocytosis in a cell thus treated may be reduced by at least about 25%, at least about 50%, at least about 75%, and may decrease phagocytosis 2-fold, 3-fold, 5-fold or more, relative to an unstimulated cell.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

FIG. 1A-1B. Activation of TLR signaling leads to enhanced PrCR of living cancer cells. (FIG. 1A) Left, a schematic showing PrCR of living tumor cells by macrophages. Blockade of CD47 leads to an imbalance of "eat me" over "don't eat me" pathways, which elicits phagocytosis of tumor cells, either Fc-dependent (elicited by Fc-FcR interaction) or Fc-independent (representing cancer-specific "eat me" signals other than Fc). Right, a phagocytosis assay showing blockade of CD47 induced phagocytosis, with SW620 cells (Control IgG-treated, anti-CD47 antibody (B6H12)-treated or CD47KO) as target cells and BMDMs from RAG2−/−, c−/−mice. Fc-receptor blocker (FcRB) reversed phagocytosis of B6H12-treated cells to the same level as that of CD47KO cells. **, P<0.01, t-test. (FIG. 1B) A phagocytosis assay showing a screen of TLR agonists, with SW620 cells (PBS-treated, anti-CD47 antibody (Hu5F9-G4)-treated or CD47KO) as target cells and BMDMs from BALB/c mice. TLR agonists used in the screen were: Pam3CSK4 (Pam, TLR1/2), Heat Killed Listeria monocytogenes (HKLM, TLR2), Poly (I:C) HMW (Poly (I:C), TLR3), Lipopolysaccharide (LPS, TLR4), Flagellin from S. typhimurium (FLA-ST, TLR5), Pam2CGDPKHPKSF (FSL-1, TLR6/2), Imiquimod (Imi, TLR7), Class B CpG oligonucleotide (ODN 1826, TLR9). Dash lines indicate 2-fold phagocytosis of each condition (PBS-treated, anti-CD47 antibody (Hu5F9-G4)-treated or CD47KO) in the control macrophage group. Error bars represent standard deviation (A and B).

(FIG. 2A) A phagocytosis assay showing a screen with combined TLR agonists and various inhibitors targeting downstream signaling molecules, with SW620 cells (control or CD47$^{KO}$) as target cells and BMDMs from RAG2+/+, γc−/− mice. Inhibitors used in the screen were: PD98059 (PD, MEK inhibitor), LY294002 (LY, PI3K inhibitor), Ibrutinib (Ibr, Btk inhibitor), YVAD (YVAD, Caspase-1 inhibitor). **, P<0.01 (t-test; Comparison between samples in control or CD47$^{KO}$ groups, Imi-ctrl vs other conditions). (FIG. 2B) Immunoblots showing the phosphorylation of Btk induced by TLR agonists (Poly (I:C) HMW, LPS, imiquimod). When cells were treated with TLR agonists and Ibrutinib simultaneously, the induction of Btk phosphorylation was attenuated. Total Btk showed no change. (FIG. 2C) and (FIG. 2D) Temporal effects of Btk activator (imiquimod) (FIG. 2C) and inhibitor (ibrutinib) (FIG. 2D) on phagocytosis, with SW620 cells$^{CD47KO}$ as target cells and BMDMs from NSG mice. Error bars represent standard deviation (FIGS. 2A, 2C and 2D).

FIG. 3A-3D. Btk controls cell surface exposure of CRT on macrophages to regulate PrCR of cancer cells. (FIG. 3A) The expression of CRT on macrophages was examined by cell surface biotinylation assay. Immunoblots showed that cell surface CRT increased upon Btk activation and decreased upon Btk inhibition. Imi: imiquimod; Ibr: ibrutinib. (FIG. 3B) Increased cell surface exposure of CRT on macrophages induced by TLR agonists (Poly (I:C) HMW, LPS, imiquimod), as examined by flow cytometry analyses. Dash lines indicate normalized phagocytic indexes of each condition (PBS-treated, anti-CD47 antibody (Hu5F9-G4)-treated or CD47$^{KO}$) in the control macrophage group. (FIG. 3D) Overexpression of CRT in J774 cells promoted phagocytosis. Expression of CRT was examined by immunoblotting. SW620 cells (Control IgG- or anti-CD47 antibody (B6H12)-treated) were used as target cells. * P<0.05, **P<0.01 (t-test). Error bars represent standard deviation (FIGS. 3C and 3D).

(FIG. 4A) A phagocytosis assay showing the effects of blocking CRT on macrophages or cancer cells. Left, a schematic showing the design of the experiments. Macrophages, target cells or both were pre-treated with CRT antibody and then subjected to phagocytosis assay. Right, a phagocytosis assay showing CRT on macrophages was necessary for phagocytosis of cancer cells, with SW620 cells (control or CD47$^{KO}$) as target cells and BMDMs from RAG2−/−, γc−/− mice. (FIG. 4B) Phagocytic ability of macrophages with differential surface CRT expression levels. Definition of CRT$^{Low}$, CRT$^{Medium}$ and CRT$^{High}$ populations were described in FIGS. 8A-B. (FIG.

4C) Normalized tumor cell phagocytosis (Y axis) were plotted against normalized cell surface CRT expression (Log 2; X axis) on macrophages, with SW620 cells (CD47$^{KO}$) as target cells and BMDMs from RAG2$^{-/-}$, γc$^{-/-}$ or NSG mice. ■: BMDMs from NSG mice treated with imiquimod for 0, 1, 6, 16, 24 hr; ▲ BMDMs from RAG2$^{-/-}$, γc$^{-/-}$ mice (CRT$^{Low}$, CRT$^{Medium}$, CRT$^{High}$ and bulk populations); * BMDMs from NSG mice (CRT$^{Low}$, CRT$^{Medium}$, CRT$^{High}$ and bulk populations). Error bars represent standard deviation (A and B).

Figure 5A:
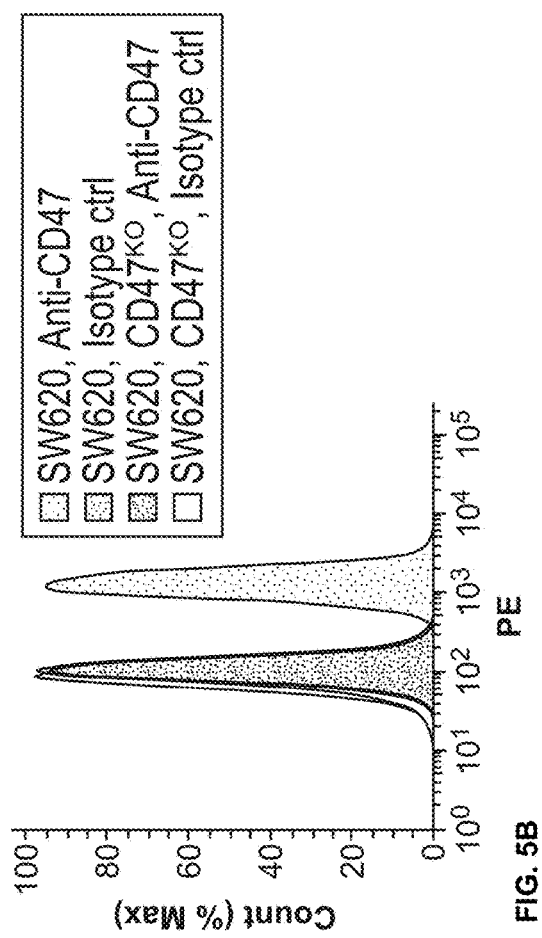
Figure 5B:
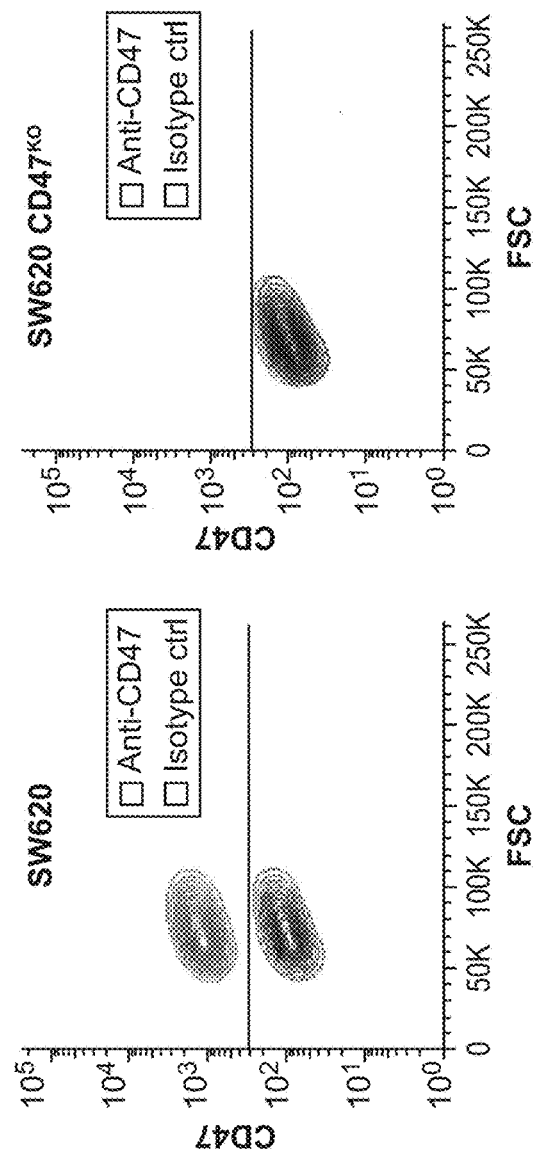

FIG. 5A-5B. TALEN-mediated CD47 knockout in SW620 cells. (FIG. 5A) and (FIG. 5B) Examination of cell surface CD47 in SW620$^{WT}$ and SW620$^{CD47KO}$ cells by flow cytometry analyses. Cells were stained with Phycoerythrin (PE) conjugated anti-CD47 antibody (B6H12) or PE-conjugated isotype control. Flow cytometry analyses were displayed in histogram (FIG. 5A) or contour (FIG. 5B).

Figure 6A:
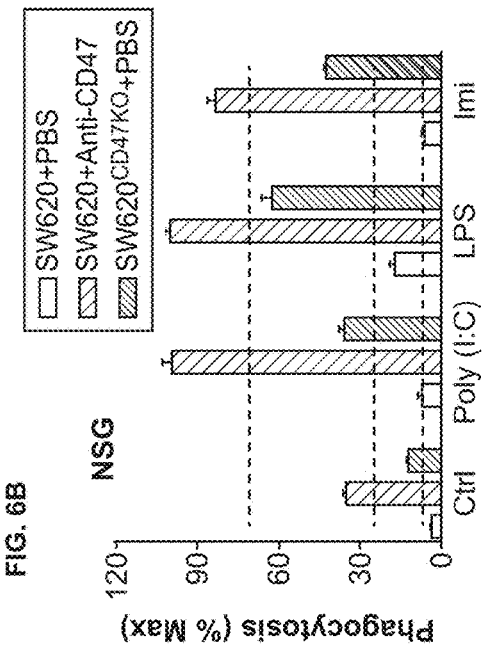
Figure 6B:
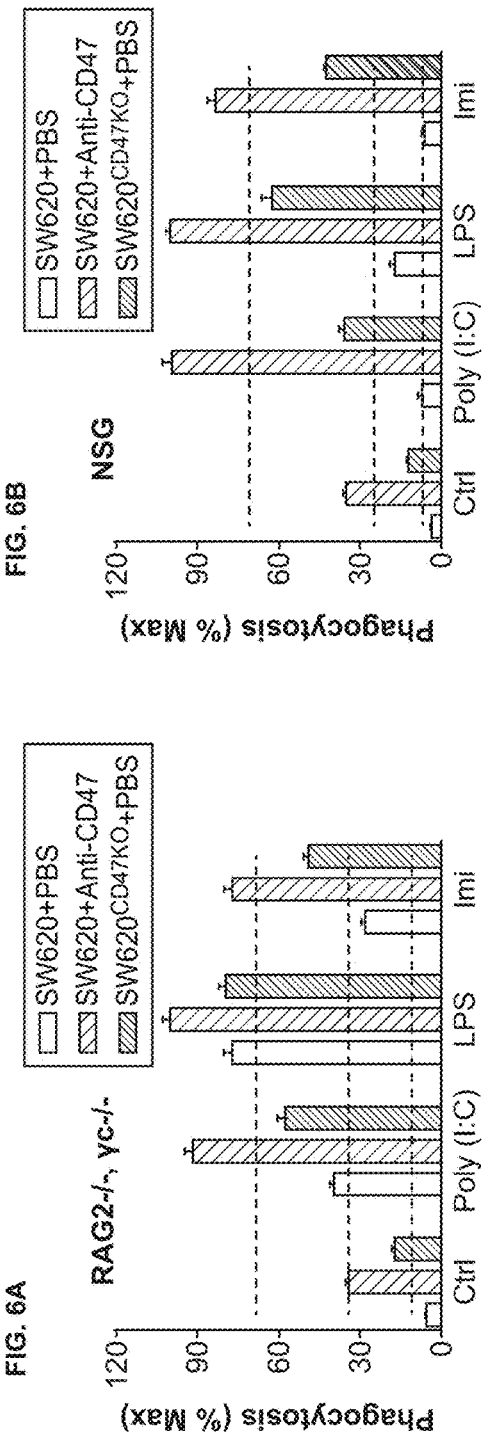
Figure 6C:
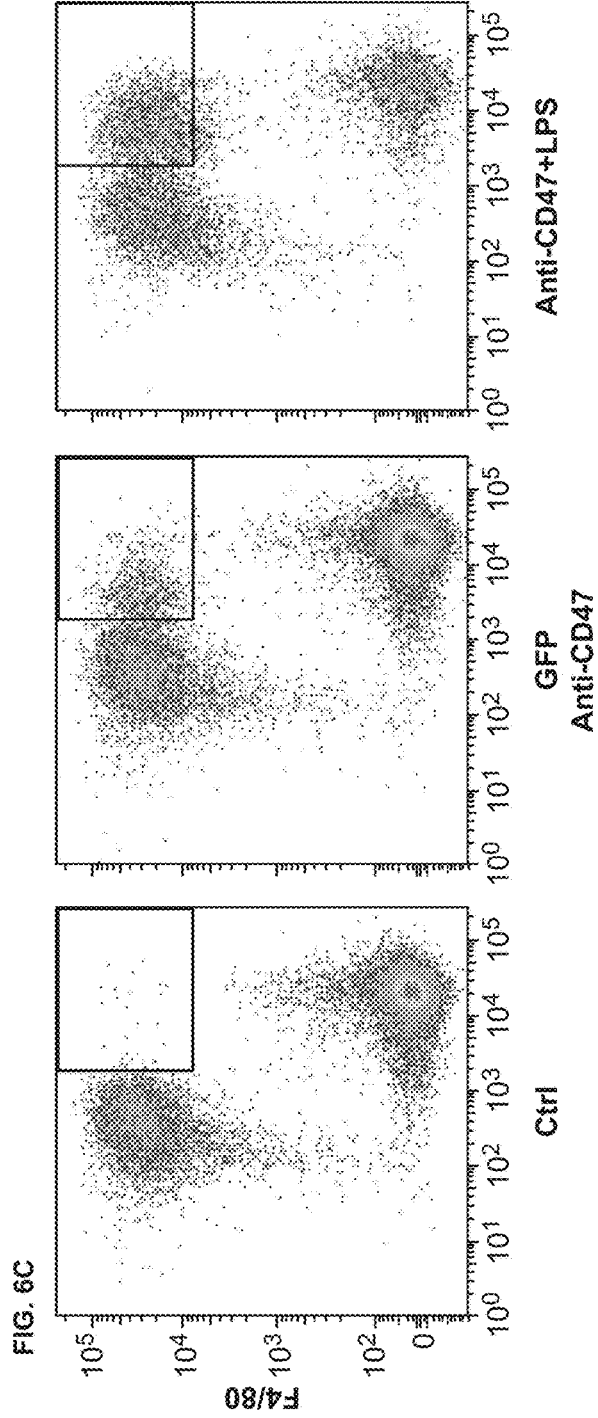

FIG. 6A-6C. Screen of TLR signaling for PRCR of tumor cells with TLR agonists. (FIG. 6A) and (FIG. 6B) Phagocytosis assays showing treatment of macrophages with TLR agonists (Poly (I:C) HMW, LPS, imiquimod) promoted phagocytosis of tumor cells, with SW620 cells (PBS-treated, anti-CD47 antibody (Hu5F9-G4)-treated or CD47$^{KO}$) as target cells and BMDMs from RAG2$^{-/-}$, γc$^{-/-}$ mice (FIG. 6A) or NSG mice (FIG. 6B). Dash lines indicate 2-fold phagocytosis of each condition (SW620+PBS, SW620+Hu5F9-G4 or SW620$^{CD47KO}$+PBS) in the control macrophage group. (FIG. 6C) Representative flow cytometry plots showing TLR agonists enhanced phagocytosis. A phagocytosis assay showing TLR agonist enhanced phagocytosis of cancer cells, with SW620 cells (PBS- or Hu5F9-G4-treated) as target cells and BMDMs from NSG mice. Phagocytosis was examined by flow cytometry analyses. Macrophages were stained with PE cy7-conjugated anti-F4/80 antibody and SW620 cells were labeled with GFP. Cells in the square of right-top corners were F4/80+GFP+ cells, representing macrophages that had phagocytosed cancer cells. Treatment of macrophages with LPS strongly enhanced their phagocytic ability. Error bars represent standard deviation (FIGS. 6A and 6B).

FIG. 7A-7D. Phagocytosis of HL60, Raji, PC-3, MDA-MB-231 is enhanced by TLR agonists. Phagocytosis assays showing TLR agonists enhanced phagocytosis of multiple human cancer cells, with different hematopoietic (HL60 and Raji) and solid tumor (PC3 and MDA-MB-231) cells (PBS- or Hu5F9-G4-treated) as target cells and BMDMs from NSG (HL60, Raji and PC3) or RAG2$^{-/-}$, γc$^{-/-}$ (MDA-MB-231) mice. HL60: Promyelocytic leukemia; Raji: Burkitt's lymphoma; PC3: Prostate cancer; MDA-MB-231: Breast cancer. Error bars represent standard deviation (FIG. 7A-7D).

Figure 8A:
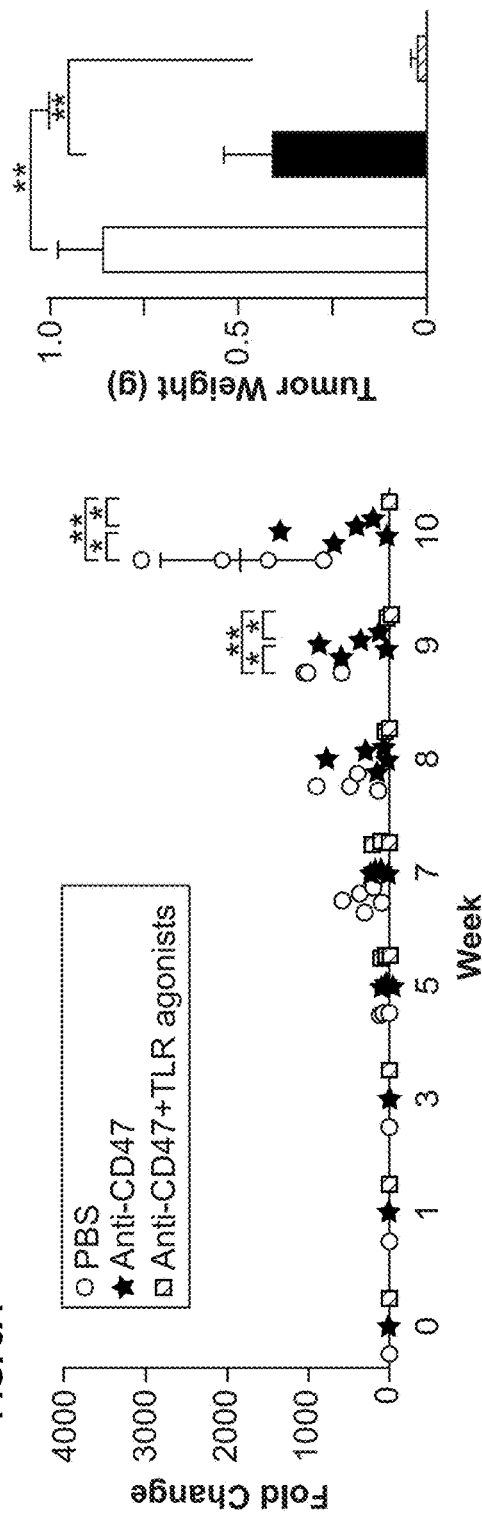
Figure 8B:
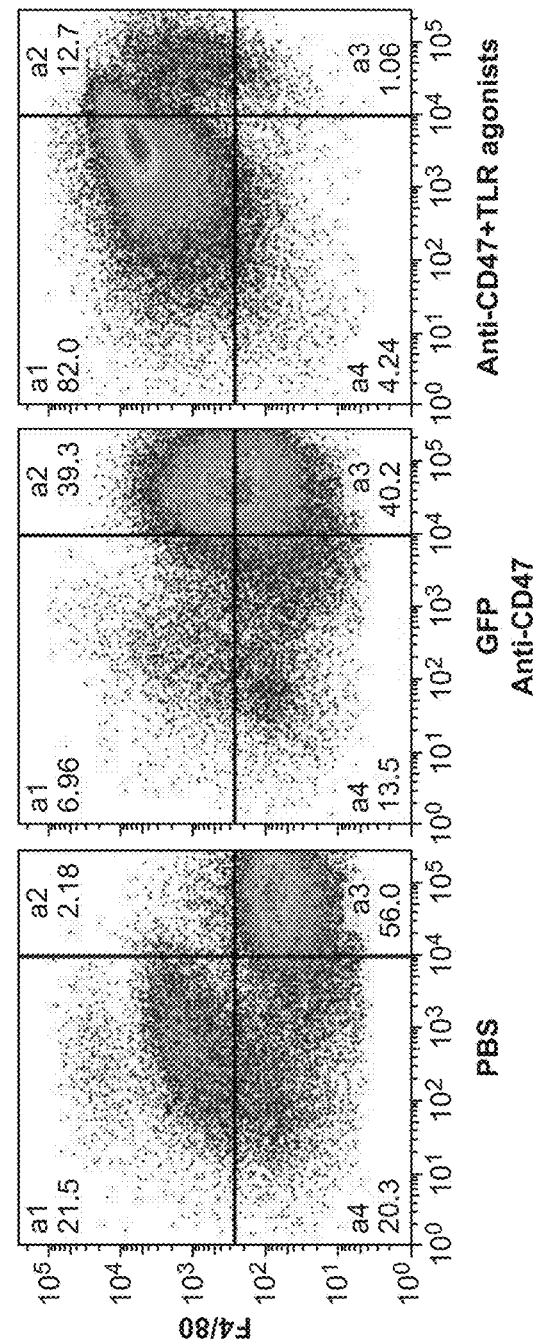

FIG. 8A-8B. TLR agonists improve the efficacy of CD47 blocking antibody to inhibit the growth of tumors in vivo. (FIG. 8A) Tumor growth monitored by bioluminescent imaging. PC3 prostate cancer cells were engrafted in NSG mice. Mice were treated with PBS, Hu5F9-G4, or Hu5F9-G4+TLR agonists (Poly (I:C) HMW+LPS) (n=5 in each group; 1 mouse in the PBS control group died due to tumor progression at week 8). TLR agonists significantly enhanced the efficacy of Hu5F9-G4 to inhibit tumor growth. (FIG. 8B) Analysis of tumor specimens by flow cytometry. Tumor specimens from each group in the experiment described in (FIG. 8A) were collected and dissociated to achieve single cell suspension. The cells were analyzed by flow cytometry. Anti-CD31 and anti-Gr-1 antibodies were used to exclude endothelial cells (CD31) and neutrophil (Gr-1). Macrophages were labeled with anti-F4/80 antibody. a4 (GFP+F4/80−) represents tumor cells, a1 (GFP-F4/80+) represents macrophages and a2 (GFP+F4/80+) represents macrophages that had phagocytosed tumor cells. Less tumor cells were observed in Hu5F9-G4 group (40%) as compared to PBS group (56%), while tumor cells were almost cleared in Hu5F9-G4+TLR agonists group (1.06%). Hu5F9-G4 group showed ongoing phagocytosis (a2) (39.3%, vs 2.18% in PBS group), while Hu5F9-G4+TLR agonists group showed largely completed phagocytosis of tumor cells (with 94.7% macrophages (a1+a2), vs 46.26% in Hu5F9-G4 group and 23.8% in PBS group). These results suggested Hu5F9-G4 enhanced the efficacy of Hu5F9-G4 in inducing PrCR of tumor cells in vivo.

FIG. 9. Expression of Btk in the hematopoietic system. A schematic showing the expression of Btk in the hematopoietic system, generated by Gene Expression Commons (5). Gene expression activity was labeled with blue (low) or red (high). Btk is expressed in all linages except for T Cells and NK cells. HSC: Hematopoietic Stem Cell; MPP: Multipotential Progenitor; GMLP: Granulo/Macrophage/Lymphoid Progenitor; pMEP/MEP: pre-/Megakaryocyte-erythroid Progenitor; CMP: Common Myeloid Progenitor; CLP: Common Lymphoid Progenitor; Plt: Platelet; Ery: Erythroid; pGMP/GMP: pre-/Granulocyte-Macrophage Progenitor; MkP: Megakaryocyte-committed Progenitor; pCFU-E: preCFU-E; Gra: Granulocyte; Mono: Monocyte; BLP: B Lymphocyte Progenitor; iNK/mNK: intermediate/mature Natural Killer Cell; BM: Bone Marrow; Spl: Spleen.

Figure 10A:
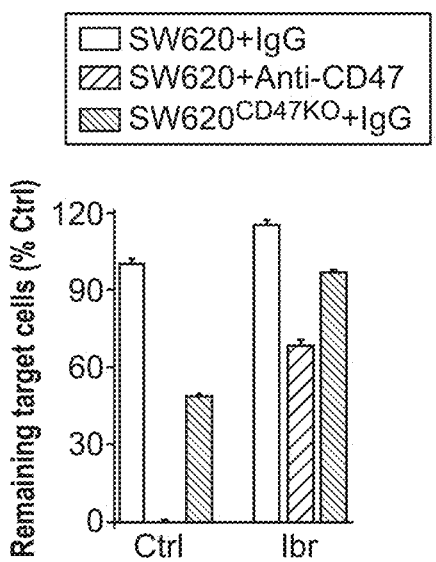
Figure 10B:
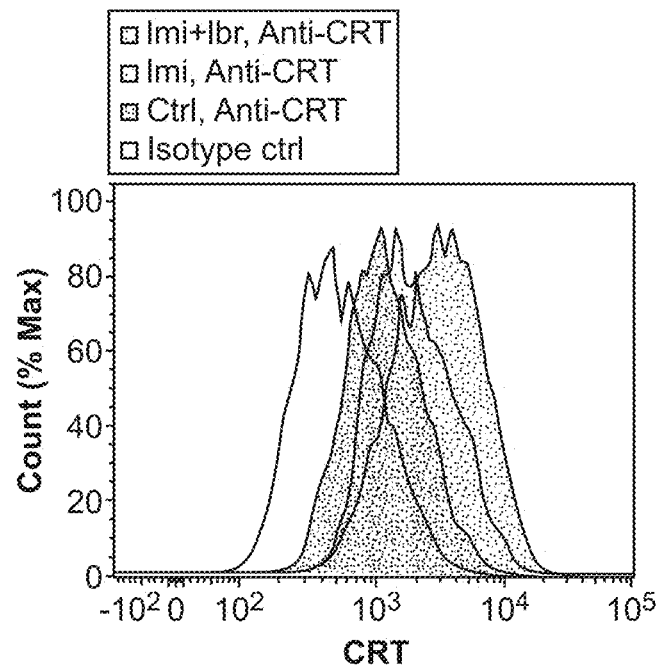
Figure 10C:
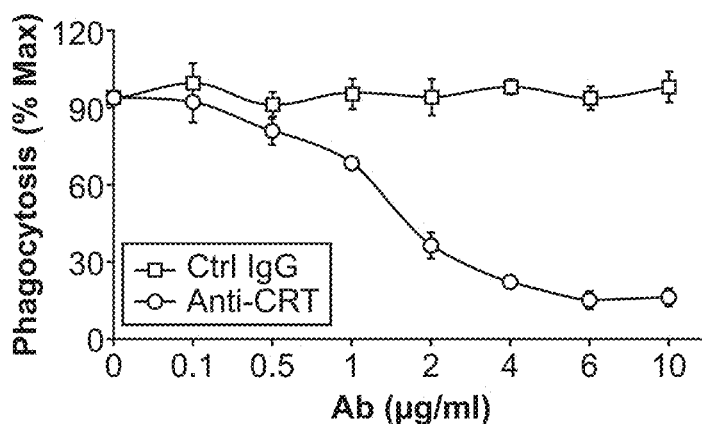
Figure 10D:
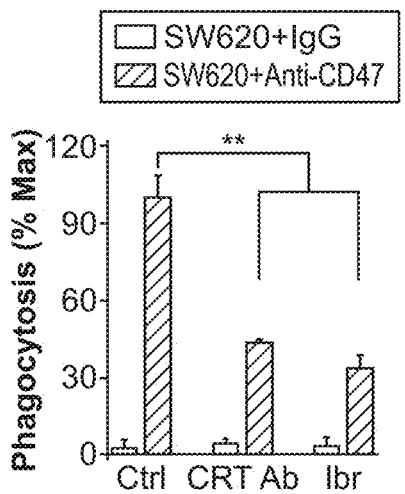

FIG. 10A-10E. Btk mediates PrCR by regulating cell surface exposure of CRT on macrophages. (FIG. 10A) Inhibition of basal level PrCR (resting macrophages) by Btk antagonism. A phagocytosis assay showing blockade of Btk inhibited tumor cell phagocytosis by resting macrophages (unstimulated by TLR signaling), with SW620 cells (Control IgG-treated, anti-CD47 antibody (B6H12)-treated or CD47$^{KO}$) as target cells and BMDMs from RAG2$^{-/-}$, γc$_{-/-}$ mice. Macrophages and target cancer cells were cocultured for 16 hr under indicated conditions, with or without Btk blocker ibrutinib. The cells were examined by flow cytometry analyses. Remaining target cells were used to evaluate efficacy of phagocytosis, with less remaining target cells representing stronger phagocytosis. Both F-dependent and Fc-independent phagocytosis induced by CD47 blockade (anti-CD47 antibody or CD47$^{KO}$) were largely reversed by Btk antagonism. (FIG. 10B) Cell surface expression of CRT was examined by flow cytometry analyses. Macrophages (ctrl, imiquimod, or imiquimod+ibrutinib) were analyzed with anti-CRT antibody. Imiquimod increased cell surface expression of CRT on macrophages and this effect was reversed by ibrutinib. (FIG. 10C) Dose response of CRT antibody in blocking phagocytosis. Dose response curves of CRT antagonism with CRT antibody or rabbit IgG (control) in blocking phagocytosis. Phagocytosis assay was performed with SW620$^{CD47KO}$ as target cells and BMDMs from RAG2$^{-/-}$, γc$_{-/-}$ mice. (FIG. 10D) A phagocytosis assay showing CRT antibody or ibrutinib inhibited phagocytosis of cancer cells, with SW620 cells (Control IgG- or anti-CD47 antibody (B6H12)-treated) as target cells and human PBMC-derived macrophages. **, P<0.01 (t-test). (FIG. 10E) Phosphorylation of CRT by Btk. Immunoblot showing CRT phosphorylation upon Btk activation. Myc-tagged CRT was expressed in J774 cells and immunoprecipitated with anti-myc antibody after imiquimod treatment. Phosphorylated CRT was detected with anti-phosphotyrosine antibody. Error bars represent standard deviation (FIGS. 10A, 10C and 10D).

FIG. 11A-11D. Induction of cell surface CRT by Btk activation is specific in macrophages. (FIG. 11A) Immunoblot of Btk expression in macrophages and cancer cells. Btk was expressed in macrophages but not in solid tumor cells. 620: SW620; 231: MDA-MB-231. (FIG. 11B-11D) Cell surface expression of CRT with or without Btk activation, as examined by flow cytometry, in macrophages (FIG. 11B), colon cancer (SW620, FIG. 11C) and breast cancer (MDA-MB-231, FIG. 11D) cells. Imi, imiquimod.

FIG. 12A-12D. Surface CRT expression on macrophages is correlated with their phagocytic abilities. (FIG. 12A) and (FIG. 12B) Macrophage sub-populations with differential cell surface CRT expression. FACS plots showing CRT expression on BMDMs from $RAG2^{-/-}$, $\gamma c_{-/-}$, $\gamma c^{-/-}$ (FIG. 12A) or NSG (FIG. 12B) mice, under control condition or imiquimod treatment. $CRT^{Low}$, $CRT^{Medium}$ and $CRT^{High}$ populations were defined and labeled as areas a, b and c. Phagocytic ability of different groups of untreated macrophages (Bulk—entire population; $CRT^{Low}$—cells in region a; $CRT^{Medium}$—cells in region b; $CRT^{High}$—cells in regions c) were showed in FIG. 4B. (FIG. 12C) Temporal effects of imiquimod (0, 1, 6, 16, 24 hr treatment) on cell surface expression of CRT on BMDMs from NSG mice, as examined by flow cytometry analysis with anti-CRT antibody. (FIG. 12D) Mean fluorescence intensity values of CRT at different time points after imiquimod treatment were normalized to the value of 0 hr and log transformed (Log 2).

FIG. 13A-13D. Cell surface expression of CRT on M1 and M2 human macrophages. (A) and (B) Differentiation of M1 (FIG. 13A) and M2 (FIG. 13B) macrophages was examined with specific markers (CD80 for M1 and CD163 for M2). (FIG. 13C) and (FIG. 13D) FACS plot showing cell surface expression of CRT on M1 and M2 macrophages.

DETAILED DESCRIPTION OF THE EMBODIMENTS

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Methods recited herein may be carried out in any order of the recited events which is logically possible, as well as the recited order of events.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

Calreticulin. Calreticulin is a multifunctional protein of 417 amino acids, molecular weight 48 kDa, that binds Ca2+ ions, rendering it inactive. The Ca2+ is bound with low affinity, but high capacity, and can be released on a signal. Calreticulin can be located in storage compartments associated with the endoplasmic reticulum, where it binds to misfolded proteins and prevents them from being exported to the Golgi apparatus. Calreticulin is also found in the nucleus, suggesting that it may have a role in transcription regulation. Calreticulin binds to the synthetic peptide SEQ ID NO: 1 KLGFFKR, which is almost identical to an amino acid sequence in the DNA-binding domain of the superfamily of nuclear receptors. The gene symbol for calreticulin is CALR, and the human sequences may be accessed at Pubmed as follows: Protein Accession #NP_004334; Nucleotide Accession #: NM 004343.

Anti-CD47 agent. As used herein, the term "anti-CD47 agent" refers to any agent that reduces the binding of CD47 (e.g., on a target cell) to SIRPα (e.g., on a phagocytic cell). Non-limiting examples of suitable anti-CD47 reagents include SIRPα reagents, including without limitation high affinity SIRPα polypeptides, anti-SIRPα antibodies, soluble CD47 polypeptides, and anti-CD47 antibodies, antibody fragments, peptides, small molecules, peptidomimetics, and the like. In some embodiments, a suitable anti-CD47 agent (e.g. an anti-CD47 antibody, a SIRPα reagent, etc.) specifically binds CD47 to reduce the binding of CD47 to SIRPα. In some embodiments, a suitable anti-CD47 agent (e.g., an anti-SIRPα antibody, a soluble CD47 polypeptide, etc.) specifically binds SIRPα to reduce the binding of CD47 to SIRPα. A suitable anti-CD47 agent that binds SIRPα does not activate SIRPα (e.g., in the SIRPα-expressing phagocytic cell).

The efficacy of a suitable anti-CD47 agent can be assessed by assaying the agent. In an exemplary assay, target cells are incubated in the presence or absence of the candidate agent. An agent for use in the methods of the invention will up-regulate phagocytosis and subsequent T cell activation by at least 10% (e.g., at least 20%, at least 30%, at least 40%, at least 50%, at least 60%, at least 70%, at least 80%, at least 90%, at least 100%, at least 120%, at least 140%, at least 160%, at least 180%, or at least 200%) compared to phagocytosis and subsequent T cell activation in the absence of the agent. Similarly, an in vitro assay for levels of tyrosine phosphorylation of SIRPα will show a decrease in phosphorylation by at least 5% (e.g., at least 10%, at least 15%, at least 20%, at least 30%, at least 40%, at least 50%, at least 60%, at least 70%, at least 80%, at least 90%, or 100%) compared to phosphorylation observed in absence of the candidate agent.

In some embodiments, the anti-CD47 agent does not activate CD47 upon binding. When CD47 is activated, a process akin to apoptosis (i.e., programmed cell death) may occur (Manna and Frazier (2004) Cancer Research 64:1026-1036). Thus, in some embodiments, the anti-CD47 agent does not directly induce cell death of a CD47-expressing cell.

SIRPα reagent. A SIRPα reagent comprises the portion of SIRPα that is sufficient to bind CD47 at a recognizable affinity, which normally lies between the signal sequence and the transmembrane domain, or a fragment thereof that retains the binding activity. A suitable SIRPα reagent reduces (e.g., blocks, prevents, etc.) the interaction between the native proteins SIRPα and CD47. The SIRPα reagent will usually comprise at least the d1 domain of SIRPα. In some embodiments, a SIRPα reagent is a fusion protein, e.g., fused in frame with a second polypeptide. In some embodiments, the second polypeptide is capable of increasing the size of the fusion protein, e.g., so that the fusion protein will not be cleared from the circulation rapidly. In some embodiments, the second polypeptide is part or whole of an immunoglobulin Fc region. The Fc region aids in phagocytosis by providing an "eat me" signal, which enhances the block of the "don't eat me" signal provided by the high affinity SIRPα reagent. In other embodiments, the second polypeptide is any suitable polypeptide that is substantially similar to Fc, e.g., providing increased size, multimerization domains, and/or additional binding or interaction with Ig molecules.

In some embodiments, a subject anti-CD47 agent is a "high affinity SIRPα reagent", which includes SIRPα-derived polypeptides and analogs thereof. High affinity SIRPα reagents are described in international application PCT/US13/21937, which is hereby specifically incorporated by reference. High affinity SIRPα reagents are variants of the native SIRPα protein. In some embodiments, a high affinity SIRPα reagent is soluble, where the polypeptide lacks the SIRPα transmembrane domain and comprises at least one amino acid change relative to the wild-type SIRPα sequence, and wherein the amino acid change increases the affinity of the SIRPα polypeptide binding to CD47, for example by decreasing the off-rate by at least 10-fold, at least 20-fold, at least 50-fold, at least 100-fold, at least 500-fold, or more.

A high affinity SIRPα reagent comprises the portion of SIRPα that is sufficient to bind CD47 at a recognizable affinity, e.g., high affinity, which normally lies between the signal sequence and the transmembrane domain, or a fragment thereof that retains the binding activity. The high affinity SIRPα reagent will usually comprise at least the d1 domain of SIRPα with modified amino acid residues to increase affinity. In some embodiments, a SIRPα variant of the present invention is a fusion protein, e.g., fused in frame with a second polypeptide. In some embodiments, the second polypeptide is capable of increasing the size of the fusion protein, e.g., so that the fusion protein will not be cleared from the circulation rapidly. In some embodiments, the second polypeptide is part or whole of an immunoglobulin Fc region. The Fc region aids in phagocytosis by providing an "eat me" signal, which enhances the block of the "don't eat me" signal provided by the high affinity SIRPα reagent. In other embodiments, the second polypeptide is any suitable polypeptide that is substantially similar to Fc, e.g., providing increased size, multimerization domains, and/or additional binding or interaction with Ig molecules. The amino acid changes that provide for increased affinity are localized in the d1 domain, and thus high affinity SIRPα reagents comprise a d1 domain of human SIRPα, with at least one amino acid change relative to the wild-type sequence within the d1 domain. Such a high affinity SIRPα reagent optionally comprises additional amino acid sequences, for example antibody Fc sequences; portions of the wild-type human SIRPα protein other than the d1 domain, including without limitation residues 150 to 374 of the native protein or fragments thereof, usually fragments contiguous with the d1 domain; and the like. High affinity SIRPα reagents may be monomeric or multimeric, i.e. dimer, trimer, tetramer, etc.

Anti-CD47 antibodies. In some embodiments, a subject anti-CD47 agent is an antibody that specifically binds CD47 (i.e., an anti-CD47 antibody) and reduces the interaction between CD47 on one cell (e.g., an infected cell) and SIRPα on another cell (e.g., a phagocytic cell). In some embodiments, a suitable anti-CD47 antibody does not activate CD47 upon binding. Non-limiting examples of suitable antibodies include clones B6H12, 5F9, 8B6, and C3 (for example as described in International Patent Publication WO 2011/143624, herein specifically incorporated by reference). Suitable anti-CD47 antibodies include fully human, humanized or chimeric versions of such antibodies. Humanized antibodies (e.g., hu5F9-G4) are especially useful for in vivo applications in humans due to their low antigenicity. Similarly caninized, felinized, etc. antibodies are especially useful for applications in dogs, cats, and other species respectively. Antibodies of interest include humanized antibodies, or caninized, felinized, equinized, bovinized, porcinized, etc., antibodies, and variants thereof.

Anti-SIRPα antibodies. In some embodiments, a subject anti-CD47 agent is an antibody that specifically binds SIRPα (i.e., an anti-SIRPα antibody) and reduces the interaction between CD47 on one cell and SIRPα on another cell. Suitable anti-SIRPα antibodies can bind SIRPα without activating or stimulating signaling through SIRPα, because activation of SIRPα would inhibit phagocytosis. Instead, suitable anti-SIRPα antibodies facilitate the phagocytosis of target cells. Thus, a suitable anti-SIRPα antibody specifically binds SIRPα (without activating/stimulating enough of a signaling response to inhibit phagocytosis) and blocks an interaction between SIRPα and CD47. Suitable anti-SIRPα antibodies include fully human, humanized or chimeric versions of such antibodies. Similarly caninized, felinized, etc. antibodies are especially useful for applications in dogs, cats, and other species respectively. Antibodies of interest include humanized antibodies, or caninized, felinized, equinized, bovinized, porcinized, etc., antibodies, and variants thereof.

Soluble CD47 polypeptides. In some embodiments, a subject anti-CD47 agent is a soluble CD47 polypeptide that specifically binds SIRPα and reduces the interaction between CD47 on one cell and SIRPα on another cell. A suitable soluble CD47 polypeptide can bind SIRPα without activating or stimulating signaling through SIRPα. Suitable soluble CD47 polypeptides facilitate the phagocytosis of target cells. Thus, a suitable soluble CD47 polypeptide specifically binds SIRPα without activating/stimulating enough of a signaling response to inhibit phagocytosis.

In some cases, a suitable soluble CD47 polypeptide can be a fusion protein (for example as structurally described in US Patent Publication US20100239579, herein specifically incorporated by reference). However, only fusion proteins that do not activate/stimulate SIRPα are suitable for the methods provided herein. Suitable soluble CD47 polypeptides also include any peptide or peptide fragment comprising variant or naturally existing CD47 sequences (e.g., extracellular domain sequences or extracellular domain variants) that can specifically bind SIRPα and inhibit the interaction between CD47 and SIRPα without stimulating enough SIRPα activity to inhibit phagocytosis.

In certain embodiments, soluble CD47 polypeptide comprises the extracellular domain of CD47, including the signal peptide (SEQ ID NO:2), such that the extracellular portion of CD47 is typically 142 amino acids in length, and has the amino acid sequence set forth in SEQ ID NO: 3. The soluble CD47 polypeptides described herein also include CD47 extracellular domain variants that comprise an amino acid sequence at least 65%-75%, 75%-80%, 80-85%, 85%-90%, or 95%-99% (or any percent identity not specifically enumerated between 65% to 100%), which variants retain the capability to bind to SIRPα without stimulating SIRPα signaling.

In certain embodiments, the signal peptide amino acid sequence may be substituted with a signal peptide amino acid sequence that is derived from another polypeptide (e.g., for example, an immunoglobulin or CTLA4). For example, unlike full-length CD47, which is a cell surface polypeptide that traverses the outer cell membrane, the soluble CD47 polypeptides are secreted; accordingly, a polynucleotide encoding a soluble CD47 polypeptide may include a nucleotide sequence encoding a signal peptide that is associated with a polypeptide that is normally secreted from a cell.

In other embodiments, the soluble CD47 polypeptide comprises an extracellular domain of CD47 that lacks the signal peptide. In an exemplary embodiment, the CD47 extracellular domain lacking the signal peptide has the amino acid sequence set forth in SEQ ID NO: 1 (124 amino acids). As described herein, signal peptides are not exposed on the cell surface of a secreted or transmembrane protein because either the signal peptide is cleaved during translocation of the protein or the signal peptide remains anchored in the outer cell membrane (such a peptide is also called a signal anchor). The signal peptide sequence of CD47 is believed to be cleaved from the precursor CD47 polypeptide in vivo.

In other embodiments, a soluble CD47 polypeptide comprises a CD47 extracellular domain variant. Such a soluble CD47 polypeptide retains the capability to bind to SIRPα without stimulating SIRPα signaling. The CD47 extracellular domain variant may have an amino acid sequence that is at least 65%-75%, 75%-80%, 80-85%, 85%-90%, or 95%-99% identical (which includes any percent identity between any one of the described ranges) to SEQ ID NO: 1.

Innate Immunity. The innate immune system is a primitive cellular response that provides for a defense of cells against pathogen antigens. Recognition of these antigens by the innate immune system may result in an inflammatory response characterized by the production of cytokines such as TNF, IL-1, IL-6, and IL-8; as well as gene activation of ICAM-1 and E-selectin, among others.

The broad classes of pathogens, e.g. viruses, bacteria, and fungi, may constitutively express a set of class-specific, mutation-resistant molecules called pathogen-associated molecular patterns (PAMPs). These microbial molecular markers may be composed of proteins, carbohydrates, lipids, nucleic acids and/or combinations thereof, and may be located internally or externally. Examples include the endotoxin lipopolysaccharide (LPS), single or double-stranded RNA, and the like.

Typically PAMP receptors (PRRs) are nonclonal, i.e. expressed on all cells of a given type, and germ-line encoded, or independent of immunologic memory. Once bound, PRRs tend to cluster, recruit other extracellular and intracellular proteins to the complex, and initiate signaling cascades that ultimately impact transcription. Further, PRRs are involved in activation of complement, coagulation, phagocytosis, inflammation, and apoptosis functions in response to pathogen detection. There are several types of PRRs including complement, glucan, mannose, scavenger, and toll-like receptors, each with specific PAMP ligands, expression patterns, signaling pathways, and anti-pathogen responses.

The Toll-like receptors are type I transmembrane (TM) PRRs that possess varying numbers of extracellular N-terminal leucine-rich repeat (LRR) motifs, followed by a cysteine-rich region, a TM domain, and an intracellular Toll/IL-1 R (TIR) motif. The LLR domain is important for ligand binding and associated signaling and is a common feature of PRRs. The TIR domain is important in protein-protein interactions and is typically associated with innate immunity. The TIR domain also unites a larger IL-1 R/TLR superfamily that is composed of three subgroups. The human TLR family is composed of at least 10 members, TLR1 through 10. Each TLR is specific in its expression patterns and PAMP sensitivities.

Toll-like receptor 3 (TLR3) recognizes double-stranded RNA (dsRNA) and mimetics thereof, a molecular pattern associated with viral infection. It maps to chromosome 4q35 and its sequence encodes a putative 904 aa protein with 24 N-terminal LRRs and a calculated molecular weight of 97 kDa. TLR3 is most closely related to TLR5, TLR7, and TLR8, each with 26% overall aa sequence identity. TLR3 mRNA is elevated after exposure to Gram-negative bacteria and to an even greater extent in response to Gram-positive bacteria.

TLR3 specifically recognizes double-stranded RNA (dsRNA) and induces multiple intracellular events responsible for innate antiviral immunity against a number of viral infections. The predicted 904-amino acid TLR3 protein contains the characteristic Toll motifs: an extracellular leucine-rich repeat (LRR) domain and a cytoplasmic interleukin-1 receptor-like region.

Exposure to double-stranded RNA (dsRNA) or polyinosine-polycytidylic acid (poly(I:C)), a synthetic dsRNA analog, induces the production of interferon α and β and by signaling through TLR3 activates NFκB. IRF3 is specifically induced by stimulation of TLR3 or TLR4, which mediates a specific gene program responsible for innate antiviral responses. TRIF is necessary for TLR3-dependent activation of NFKB. It serves as an adaptor protein linking RIP1 and TLR3 to mediate TLR3-induced NFKB activation.

Toll-like receptor 4 is a protein that in humans is encoded by the TLR4 gene. It detects lipopolysaccharide from Gram-negative bacteria and is thus important in the activation of the innate immune system. This receptor is most abundantly expressed in placenta, and in myelomonocytic subpopulation of the leukocytes. The human TLR4 gene may be accessed at Genbank NM_003266.3 and the protein accessed at Genbank NP_003257.1.

Activation of TLR4 leads to downstream release of inflammatory modulators including TNF-α and Interleukin- 1. Agonists include morphine, oxycodone, fentanyl, methadone, lipopolysaccharides (LPS), carbamazepine, oxcarbazepine, etc.

TLR agonist. TLR agonists activate TLRs, including without limitation TLR3, TLR4, and RIG1. Examples of TLR agonists include pathogen-associated molecular patterns (PAMPs) and mimetics thereof. These microbial molecular markers may be composed of proteins, carbohydrates, lipids, nucleic acids and/or combinations thereof, and may be located internally or externally, as known in the art. Examples include LPS, zymosan, peptidoglycans, flagellin, synthetic TLR2 agonist Pam3cys, Pam3CSK4, MALP-2, Imiquimod, CpG ODN, and the like.

TLR3 agonists include double-stranded RNA; Poly(I:C), Poly(A.U), etc., where such nucleic acids usually have a size of at least about 10 bp, at least about 20 bp, at least about 50 bp and may have a high molecular weight of from about 1 to about 20 kb, usually not more than about 50 to 100 kb. Alternative TLR3 agonists may directly bind to the protein, e.g. antibodies or small molecules that selectively bind to and activate TLR3. Other TLR3 agonists include retroviruses, e.g. a retrovirus engineered to lack the ability to integrate into the genome.

The dose of agonist that is effective in the methods of the invention is a dose that increases the expression of CRT on a phagocytic cell or cell population, relative to the same population in the absence of the TLR agonist.

For example, where the TLR agonist of poly I:C or an analog thereof, an effective dose may be at least about 10 ng/ml, at least about 50 ng/ml, at least about 100 ng/ml, at least about 250 ng/ml, at least about 500 ng/ml. The dose of a TLR agonist other than poly I:C may be calculated based on the provision of activity equivalent to the optimized poly I:C dose.

TLR3, 4, 7/8 and 9 agonists are of particular interest as immunotherapeutic agents to treat cancer. Included in the group are, without limitation: 852A: Synthetic imidazoquinoline mimicking viral ssRNA; VTX-2337: Small-molecule selective TLR8 agonist mimicking viral ssRNA; BCG: *Bacillus* of Calmette-Guerin, *Mycobacterium bovis*; CpG ODN: CpG oligodeoxynucleotide; Imiquimod: Synthetic imidazoquinoline mimicking viral ssRNA; LPS: Lipopolysaccharide; MPL: Monophosphoryl lipid A; Poly I:C: Polyriboinosinic-polyribocytidylic acid; PolyICLC: Poly I:C-poly-1-lysine; Resiquimod: Synthetic imidazoquinoline mimicking viral ssRNA.

Imiquimod is a synthetic imidazoquinoline that targets TLR7. A newer imidazoquinoline TLR7 agonist, 852A, administered parenterally as monotherapy has shown modest clinical efficacy with disease stabilization as a monotherapy. Resiquimod is an imidazoquinoline TLR7/8 agonist in humans.

CpG are single-strand oligodeoxynucleotides (ODNs), characterized by motifs containing cytosines and guanines. Based on their immunologic effects, CpG ODNs are divided into three different classes: CpG-A, a potent stimulator of NK cells owing to its IFN-α-producing effect on pDCs; CpG-B, a moderate IFN-α inducer, and enhancer of antigen-specific immune responses (upregulates costimulatory molecules on pDCs and B cells, induces Th1 cytokine production and stimulates antigen presentation by pDCs); and CpG-C, which combines the stimulatory capacity of both CpG-A and CpG-B. CpG 7909 (PF-3512676, a CpG type B and TLR9 agonist) has been evaluated in several tumor types including renal cell carcinoma, glioblastoma, melanoma, cutaneous T-cell lymphoma and non-Hodgkin's lymphoma.

Polyriboinosinic-polyribocytidylic acid (Poly I:C) is a synthetic analog of viral dsRNA that stimulates endosomal (TLR3) and/or cytosolic melanoma differentiation-associated gene 5 (MDA5), leading to increased production of type I IFNs.

Lipid A molecules that target the TLR4 complex include monophosphoryl lipid A (MPL), a derivative of lipid A from *Salmonella minnesota*.

Bruton's tyrosine kinase (Btk) contains a PH domain that binds phosphatidylinositol (3,4,5)-trisphosphate (PIP3). PIP3 binding induces Btk to phosphorylate phospholipase C, which in turn hydrolyzes PIP2, a phosphatidylinositol, into two second messengers, inositol triphosphate (IP3) and diacylglycerol (DAG), which then go on to modulate the activity of downstream proteins during B-cell signalling. Mutations in the BTK gene are implicated in the primary immunodeficiency disease X-linked agammaglobulinemia (Bruton's agammaglobulinemia). Patients with XLA have normal pre-B cell populations in their bone marrow but these cells fail to mature and enter the circulation. Ibrutinib (PCI-32765), is a selective Bruton's tyrosine kinase inhibitor.

Ibrutinib (1-[(3R)-3-[4-amino-3-(4-phenoxyphenyl)pyrazolo[3,4-d]pyrimidin-1-yl]piperidin-1-yl]prop-2-en-1-one) is a specific inhibitor of Btk. In the methods of the present invention, it may be administered, e.g. in an oral dosage form, at a dose of from about 10 mg/day, about 50 mg/day, about 100 mg/day, about 250 mg/day, about 350 mg/day, about 420 mg/day, about 500 mg/day, about 600 mg/day and not more than about 1000 mg/day. Administration may be continued until unacceptable toxicity or disease progression.

Phagocytic antigen presenting cell. The terms "phagocytic cells" and "phagocytes" are used interchangeably herein to refer to a cell that is capable of phagocytosis, i.e. engulfing a large particulate mass, for example from about 0.1 μm in diameter up to about 2 mm or about 1 mm in diameter; from about 0.5 μm in diameter in to about 1 mm in diameter, etc, particularly including up to the size of a mammalian cell, e.g. a tumor cell. Phagocytosis in this context is defined by the engulfment of cells, pathogens, and various particles by surrounding it with the effector cell membrane.

There are several categories of phagocytes: macrophages; mononuclear cells (histiocytes and monocytes); polymorphonuclear leukocytes; (neutrophils) and dendritic cells. Macrophages are of particular interest. Phagocytosis-associated cell responses include immunomodulatory responses like the generation and release of pro-inflammatory and anti-inflammatory mediators, and also cell responses of destructive nature such as the respiratory burst, and the release of toxic and microbicidal molecules by degranulation. Professional phagocytes are capable of recognizing a wide variety of phagocytic targets, and of ingesting them at a higher rate than non-phagocytic cells.

Neutrophils and macrophages are representative of fully differentiated phagocytes. While neutrophils leaving the bone marrow are fully differentiated, macrophages differentiate from circulating monocytes in extra-vascular tissues. Monocytes display a lower phagocytic response, compared to neutrophils and macrophages, and must respond to activation and differentiation signals in order to achieve optimal phagocytic capacity. The process of monocyte-to-macrophage differentiation has been well characterized, and can be performed in vitro or in vivo.

A "therapeutically effective dose" or "therapeutic dose" is an amount sufficient to effect desired clinical results (i.e., achieve therapeutic efficacy). For some purposes in the present invention, an effective dose of an anti-CD47 agent is the dose that increases phagocytosis by at least about 10%, at least about 20%, at least about 50%, at least about 75%, at least about 100%, up to 2-fold, 3-fold or more.

For purposes of this invention, a therapeutically effective dose of an anti-CD47 agent is an amount that is sufficient to palliate, ameliorate, stabilize, reverse, prevent, slow or delay the progression of the disease state (e.g., cancer or chronic infection) by increasing macrophage mediated killing of a target cell. Thus, a therapeutically effective dose of an anti-CD47 agent can decrease the target cell population through an in vivo immune response by at least about 10%, at least about 20%, at least about 50%, at least about 75%, at least about 90% or more, relative to the effect in the absence of administering a loaded population of phAPC.

Myelodysplastic syndromes. The myelodysplastic syndromes (also known as MDS or myelodysplasia) are hematological (i.e., blood-related) medical conditions with ineffective development (or "dysplasia") of blood cells. Patients with MDS can develop severe anemia and require blood transfusions. In some cases, the disease worsens and the patient develops cytopenias (low blood counts) caused by progressive bone marrow failure. The outlook in MDS depends on the type and severity.

Included as types of MDS that can be treated by the methods of the invention is refractory anemia; refractory anemia with ring sideroblasts; refractory anemia with excess blasts; refractory cytopenia with multilineage dysplasia; refractory cytopenia with unilineage dysplasia; unclassifiable myelodysplastic syndrome; myelodysplastic syndrome associated with an isolated del(5q) chromosome abnormality; chronic myelomonocytic leukemia (CMML).

Autoimmune hemolytic anemia (AIHA) is defined as an increased destruction of erythrocytes due to the presence of anti-erythrocyte autoantibodies (AEA) and can be classified as either autoimmune, alloimmune, or drug-induced depending on the type of antigen giving rise to the immune response. General hemolytic anemia is estimated to occur in about 4 cases per 1000 per year, but for AIHA the annual incidence is estimated to about 1-3 cases per 100,000 per year. AIHA can appear either as a primary disease or, in about 20-80% of the cases, secondary to other autoimmune diseases, lymphoid malignancies, infections, immunodeficiencies, or tumors, where lymphoid malignancies are the most common reasons for secondary AIHA. AEA are classified as cold or warm autoantibodies, as they react optimally at temperatures below 30° C. or at 35° C. to 40° C. respectively. Warm AEA are mostly IgG but sometimes IgA and/or IgM are also present, and are responsible for about 50-70% of AIHA cases. The binding of warm IgG AEA to erythrocytes does not itself damage the erythrocytes, since erythrocyte bound IgG, in contrast to surface bound IgM, is a poor activator of the classical complement pathway. Instead, surface bound IgG is usually recognized by Fcγ receptors of cells of the monocyte-macrophage phagocytic system, preferentially in the spleen and liver, resulting in uptake and destruction of IgG-opsonized erythrocytes. However, macrophage-mediated elimination of erythrocytes in AIHA is likely to be mediated by synergistic activity of macrophage Fcγ and complement receptors (recognizing complement factors C3b and $C3b_i$), since erythrocytes opsonized with very low levels of IgG are not eliminated in vivo in the absence of complement. Furthermore, low levels of complement opsonization does not result in erythrocyte phagocytosis in the absence of IgG, whereas low levels of both complement and IgG-opsonization can induce efficient erythrocyte phagocytosis both in vivo and in vitro.

Immune thrombocytopenic purpura (ITP) is an autoimmune disease characterised by low platelet counts due to antibody-mediated destruction of platelets by macrophages. ITP is classified as acute or chronic, where acute ITP has a rapid onset with typical petechiae and bruises, is often preceded by an infectious illness, mainly affects young children, and normally resolves spontaneously within six months. Chronic ITP often has an adult onset that is more insidious than the acute form and is about two to three times as common among women as among men.

A positive anti-platelet autoantibody test is found in about 70-80% of adults with ITP and in children with chronic ITP. Platelet autoantibodies are of the IgG type and are mostly directed to platelet membrane glycoproteins, including GPIIb/IIIa, GPIb-IX, and GPIa-IIa. Platelets coated with IgG autoantibodies undergo accelerated clearance through Fcγ receptor-mediated phagocytosis by macrophages, preferably in the spleen and liver. Most patients have antibodies directed to several different platelet surface proteins. Adults with diagnosed ITP are conventionally initially treated with corticosteroids. Intravenous gammaglobulin (IVIG) is another common approach in treatment of ITP, particularly for treatment of internal bleedings. IVIG has well known anti-inflammatory effects, generally attributed to the immunoglobulin G (IgG) Fc domain, which is thought to block pro-phagocytic Fc receptors on macrophages.

The term "antibody" or "antibody moiety" is intended to include any polypeptide chain-containing molecular structure with a specific shape that fits to and recognizes an epitope, where one or more non-covalent binding interactions stabilize the complex between the molecular structure and the epitope. Antibodies utilized in the present invention may be polyclonal antibodies, although monoclonal antibodies are preferred because they may be reproduced by cell culture or recombinantly, and can be modified to reduce their antigenicity.

The phrase "bispecific antibody" refers to a synthetic or recombinant antibody that recognizes more than one protein. Examples include bispecific antibodies 2B1, 520C9xH22, mDX-H210, and MDX447. Bispecific antibodies directed against a combination of epitopes, will allow for the targeting and/or depletion of cellular populations expressing the combination of epitopes.

Polyclonal antibodies can be raised by a standard protocol by injecting a production animal with an antigenic composition. See, e.g., Harlow and Lane, Antibodies: A Laboratory Manual, Cold Spring Harbor Laboratory, 1988. When utilizing an entire protein, or a larger section of the protein, antibodies may be raised by immunizing the production animal with the protein and a suitable adjuvant (e.g., Freund's, Freund's complete, oil-in-water emulsions, etc.) When a smaller peptide is utilized, it is advantageous to conjugate the peptide with a larger molecule to make an immunostimulatory conjugate. Commonly utilized conjugate proteins that are commercially available for such use include bovine serum albumin (BSA) and keyhole limpet hemocyanin (KLH). In order to raise antibodies to particular epitopes, peptides derived from the full sequence may be utilized. Alternatively, in order to generate antibodies to relatively short peptide portions of the protein target, a superior immune response may be elicited if the polypeptide is joined to a carrier protein, such as ovalbumin, BSA or KLH.

Alternatively, for monoclonal antibodies, hybridomas may be formed by isolating the stimulated immune cells, such as those from the spleen of the inoculated animal. These cells are then fused to immortalized cells, such as myeloma cells or transformed cells, which are capable of replicating indefinitely in cell culture, thereby producing an immortal, immunoglobulin-secreting cell line. In addition, the antibodies or antigen binding fragments may be produced by genetic engineering. Humanized, chimeric, or xenogeneic human antibodies, which produce less of an immune response when administered to humans, are preferred for use in the present invention.

Antibodies that have a reduced propensity to induce a violent or detrimental immune response in humans (such as anaphylactic shock), and which also exhibit a reduced propensity for priming an immune response which would prevent repeated dosage with the antibody therapeutic or imaging agent are preferred for use in the invention. These antibodies are preferred for all administrative routes. Thus, humanized, chimeric, or xenogenic human antibodies, which produce less of an immune response when administered to humans, are preferred for use in the present invention.

Chimeric antibodies may be made by recombinant means by combining the murine variable light and heavy chain regions (VK and VH), obtained from a murine (or other animal-derived) hybridoma clone, with the human constant light and heavy chain regions, in order to produce an antibody with predominantly human domains. The production of such chimeric antibodies is well known in the art, and may be achieved by standard means (as described, e.g., in U.S. Pat. No. 5,624,659, incorporated fully herein by reference). Humanized antibodies are engineered to contain even more human-like immunoglobulin domains, and incorporate only the complementarity-determining regions of the animal-derived antibody. This is accomplished by carefully examining the sequence of the hyper-variable loops of the variable regions of the monoclonal antibody, and fitting them to the structure of the human antibody chains. Although facially complex, the process is straightforward in practice. See, e.g., U.S. Pat. No. 6,187,287, incorporated fully herein by reference. Alternatively, single chain antibodies (Fv, as described below) can be produced from phage libraries containing human variable regions. See U.S. Pat. No. 6,174,708, incorporated fully herein by reference.

In addition to entire immunoglobulins (or their recombinant counterparts), immunoglobulin fragments comprising the epitope binding site (e.g., Fab', F(ab')$_2$, or other fragments) are useful as antibody moieties in the present invention. Such antibody fragments may be generated from whole immunoglobulins by ficin, pepsin, papain, or other protease cleavage. "Fragment" or minimal immunoglobulins may be designed utilizing recombinant immunoglobulin techniques. For instance "Fv" immunoglobulins for use in the present invention may be produced by linking a variable light chain region to a variable heavy chain region via a peptide linker (e.g., poly-glycine or another sequence which does not form an alpha helix or beta sheet motif).

Fv fragments are heterodimers of the variable heavy chain domain ($V_H$) and the variable light chain domain ($V_L$). The heterodimers of heavy and light chain domains that occur in whole IgG, for example, are connected by a disulfide bond. Recombinant Fvs in which $V_H$ and $V_L$ are connected by a peptide linker are typically stable, see, for example, Huston et al., Proc. Natl. Acad, Sci. USA 85:5879-5883 (1988) and Bird et al., Science 242:423-426 (1988), both fully incorporated herein, by reference. These are single chain Fvs which have been found to retain specificity and affinity and have been shown to be useful for imaging tumors and to make recombinant immunotoxins for tumor therapy. Any of these minimal antibodies may be utilized in the present invention, and those which are humanized to avoid HAMA reactions are preferred for use in embodiments of the invention.

In addition, derivatized immunoglobulins with added chemical linkers, detectable moieties, e.g. fluorescent dyes, enzymes, radioisotopes, substrates, chemiluminescent moieties, or specific binding moieties, e.g. streptavidin, avidin, biotin, etc. may be utilized in the methods and compositions of the present invention. For convenience, the term "antibody" or "antibody moiety" will be used throughout to generally refer to molecules which specifically bind to an epitope of the targeted protein, although the term will encompass all immunoglobulins, derivatives, fragments, recombinant or engineered immunoglobulins, and modified immunoglobulins, as described above.

Candidate binding agents can be tested for activity by any suitable standard means. As a first screen, the antibodies may be tested for binding against the target antigen utilized to produce them. As a second screen, candidate agents may be tested for binding to an appropriate cell, e.g. cancer cell, hematopoietic cell, etc. For these screens, the candidate antibody may be labeled for detection (e.g., with fluorescein or another fluorescent moiety, or with an enzyme such as horseradish peroxidase). After selective binding to the target is established, the candidate agent may be tested for appropriate activity (i.e., the ability to decrease tumor cell growth and/or to aid in visualizing tumor cells) in an in vivo model.

By "manipulating phagocytosis" is meant an up-regulation or a down-regulation in phagocytosis by at least about 10%, or up to 20%, or 50%, or 70% or 80% or up to about 90% compared to level of phagocytosis observed in absence of intervention. Thus in the context of decreasing phagocytosis of circulating hematopoietic cells, particularly in a transplantation context, manipulating phagocytosis means a down-regulation in phagocytosis by at least about 10%, or up to 20%, or 50%, or 70% or 80% or up to about 90% compared to level of phagocytosis observed in absence of intervention.

The terms "phagocytic cells" and "phagocytes" are used interchangeably herein to refer to a cell that is capable of phagocytosis. There are three main categories of phagocytes: macrophages, mononuclear cells (histiocytes and monocytes); polymorphonuclear leukocytes (neutrophils) and dendritic cells.

The term "biological sample" encompasses a variety of sample types obtained from an organism and can be used in a diagnostic or monitoring assay. The term encompasses blood and other liquid samples of biological origin, solid tissue samples, such as a biopsy specimen or tissue cultures or cells derived therefrom and the progeny thereof. The term encompasses samples that have been manipulated in any way after their procurement, such as by treatment with reagents, solubilization, or enrichment for certain components. The term encompasses a clinical sample, and also includes cells in cell culture, cell supernatants, cell lysates, serum, plasma, biological fluids, and tissue samples.

The terms "cancer," "neoplasm," and "tumor" are used interchangeably herein to refer to cells which exhibit autonomous, unregulated growth, such that they exhibit an aberrant growth phenotype characterized by a significant loss of control over cell proliferation. Cells of interest for detection, analysis, or treatment in the present application include precancerous (e.g., benign), malignant, pre-metastatic, metastatic, and non-metastatic cells. Cancers of virtually every tissue are known. The phrase "cancer burden" refers to the quantum of cancer cells or cancer volume in a subject. Reducing cancer burden accordingly refers to reducing the number of cancer cells or the cancer volume in a subject. The term "cancer cell" as used herein refers to any cell that is a cancer cell or is derived from a cancer cell e.g. clone of a cancer cell. Many types of cancers are known to those of skill in the art, including solid tumors such as carcinomas, sarcomas, glioblastomas, melanomas, lymphomas, myelomas, etc., and circulating cancers such as leukemias. Examples of cancer include but are not limited to, ovarian cancer, breast cancer, colon cancer, lung cancer, prostate cancer, hepatocellular cancer, gastric cancer, pancreatic cancer, cervical cancer, ovarian cancer, liver cancer, bladder cancer, cancer of the urinary tract, thyroid cancer, renal cancer, carcinoma, melanoma, head and neck cancer, and brain cancer.

The "pathology" of cancer includes all phenomena that compromise the well-being of the patient. This includes, without limitation, abnormal or uncontrollable cell growth, metastasis, interference with the normal functioning of neighboring cells, release of cytokines or other secretory products at abnormal levels, suppression or aggravation of inflammatory or immunological response, neoplasia, premalignancy, malignancy, invasion of surrounding or distant tissues or organs, such as lymph nodes, etc.

As used herein, the terms "cancer recurrence" and "tumor recurrence," and grammatical variants thereof, refer to further growth of neoplastic or cancerous cells after diagnosis of cancer. Particularly, recurrence may occur when further cancerous cell growth occurs in the cancerous tissue. "Tumor spread," similarly, occurs when the cells of a tumor disseminate into local or distant tissues and organs; therefore tumor spread encompasses tumor metastasis. "Tumor invasion" occurs when the tumor growth spread out locally to compromise the function of involved tissues by compression, destruction, or prevention of normal organ function.

As used herein, the term "metastasis" refers to the growth of a cancerous tumor in an organ or body part, which is not directly connected to the organ of the original cancerous tumor. Metastasis will be understood to include micrometastasis, which is the presence of an undetectable amount of cancerous cells in an organ or body part which is not directly connected to the organ of the original cancerous tumor. Metastasis can also be defined as several steps of a process, such as the departure of cancer cells from an original tumor site, and migration and/or invasion of cancer cells to other parts of the body.

The terms "treatment", "treating", "treat" and the like are used herein to generally refer to obtaining a desired pharmacologic and/or physiologic effect. The effect may be prophylactic in terms of completely or partially preventing a disease or symptom thereof and/or may be therapeutic in terms of a partial or complete stabilization or cure for a disease and/or adverse effect attributable to the disease. "Treatment" as used herein covers any treatment of a disease in a mammal, particularly a human, and includes: (a) preventing the disease or symptom from occurring in a subject which may be predisposed to the disease or symptom but has not yet been diagnosed as having it; (b) inhibiting the disease symptom, i.e., arresting its development; or (c) relieving the disease symptom, i.e., causing regression of the disease or symptom.

The terms "recipient", "individual", "subject", "host", and "patient", used interchangeably herein and refer to any mammalian subject for whom diagnosis, treatment, or therapy is desired, particularly humans.

A "host cell", as used herein, refers to a microorganism or a eukaryotic cell or cell line cultured as a unicellular entity which can be, or has been, used as a recipient for a recombinant vector or other transfer polynucleotides, and include the progeny of the original cell which has been transfected. It is understood that the progeny of a single cell may not necessarily be completely identical in morphology or in genomic or total DNA complement as the original parent, due to natural, accidental, or deliberate mutation.

"Therapeutic target" refers to a gene or gene product that, upon modulation of its activity (e.g., by modulation of expression, biological activity, and the like), can provide for modulation of the cancerous phenotype. As used throughout, "modulation" is meant to refer to an increase or a decrease in the indicated phenomenon (e.g., modulation of a biological activity refers to an increase in a biological activity or a decrease in a biological activity).

"Reducing growth of cancer cells" includes, but is not limited to, reducing proliferation of cancer cells, and reducing the incidence of a non-cancerous cell becoming a cancerous cell. Whether a reduction in cancer cell growth has been achieved can be readily determined using any known assay, including, but not limited to, [$^3$H]-thymidine incorporation; counting cell number over a period of time; detecting and/or measuring a marker associated with the cancer, etc.

Whether a substance, or a specific amount of the substance, is effective in treating cancer can be assessed using any of a variety of known diagnostic assays for cancer, including, but not limited to biopsy, contrast radiographic studies, CAT scan, and detection of a tumor marker associated with cancer in the blood of the individual. The substance can be administered systemically or locally, usually systemically.

In certain embodiments, a bi-specific antibody may be used. For example a bi-specific antibody in which one antigen binding domain is directed against CTR and the other antigen binding domain is directed against a cancer cell marker, such as CD47, EGFR; HER2; CD96, CD97, CD99, PTHR2, HAVCR2 etc.

For administration, the active agents will be mixed, prior to administration, with a non-toxic, pharmaceutically acceptable carrier substance. Usually, this will be an aqueous solution, such as normal saline or phosphate-buffered saline (PBS), Ringer's solution, lactate-Ringer's solution, or any isotonic physiologically acceptable solution for administration by the chosen means. Preferably, the solution is sterile and pyrogen-free, and is manufactured and packaged under current Good Manufacturing Processes (GMPs), as approved by the FDA. The clinician of ordinary skill is familiar with appropriate ranges for pH, tonicity, and additives or preservatives when formulating pharmaceutical compositions for administration by intravascular injection, intrathecal injection, injection into the cerebro-spinal fluid, direct injection into the tumor, or by other routes. In addition to additives for adjusting pH or tonicity, the antibody-therapeutics and antibody-imaging agents may be stabilized against aggregation and polymerization with amino acids and non-ionic detergents, polysorbate, and polyethylene glycol. Optionally, additional stabilizers may include various physiologically-acceptable carbohydrates and salts. Also, polyvinylpyrrolidone may be added in addition to the amino acid. Suitable therapeutic immunoglobulin solutions which are stabilized for storage and administration to humans are described in U.S. Pat. No. 5,945,098, incorporated fully herein by reference. Other agents, such as human serum albumin (HSA), may be added to the therapeutic or imaging composition to stabilize the antibody conjugates.

The compositions of the invention may be administered using any medically appropriate procedure, e.g., intravascular (intravenous, intraarterial, intracapillary) administration, injection into the cerebrospinal fluid, intracavity, subcutaneously, or direct injection in the tumor. For the imaging compositions of the invention, administration via intravascular injection is preferred for pre-operative visualization of the tumor.

The effective amount of the active agents to be given to a particular patient will depend on a variety of factors, several of which will be different from patient to patient. A competent clinician will be able to determine an effective amount to administer to a patient to retard the growth and promote the death of tumor cells, or an effective amount of an imaging composition to administer to a patient to treatment myelodysplastic syndrome. Dosage will depend on the treatment of the tumor, route of administration, the nature of the therapeutics, sensitivity of the tumor to the therapeutics, etc. Utilizing $LD_{50}$ animal data, and other information available for the agents, a clinician can determine the maximum safe dose for an individual, depending on the route of administration. For instance, an intravenously administered dose may be more than an intrathecally administered dose, given the greater body of fluid into which the therapeutic composition is being administered. Similarly, compositions which are rapidly cleared from the body may be administered at higher doses, or in repeated doses, in order to maintain a therapeutic concentration. Imaging moieties are typically less toxic than cytotoxic moieties and may be administered in higher doses in some embodiments. Utilizing ordinary skill, the competent clinician will be able to optimize the dosage of a particular therapeutic composition in the course of routine clinical trials.

Typically the dosage will be 0.001 to 100 milligrams per kilogram subject body weight. The agents can be administered to the subject in a series of more than one administration. For therapeutic compositions, regular periodic administration (e.g., every 2-3 days) will sometimes be required, or may be desirable to reduce toxicity. For therapeutic compositions which will be utilized in repeated-dose regimens, agents which do not provoke HAMA or other immune responses are preferred.

Methods of Use

Methods are provided for the treatment of cancer. An activator of TLR signaling or a BTK agonist is provided in combination with CD47 blockade, where the removal of cancer cells is increased relative to the cell removal in the presence of either agent as a monotherapy. In some embodiments, a population of cells comprising macrophages is contacted in vitro or in vivo with a dose of a TLR agonist or a BTK agonist that is effective in increasing CRT on the cell surface of the macrophage by at least about 25%, at least about 50%, at least about 75%, and may increase expression 2-fold, 3-fold, 5-fold or more, relative to an unstimulated cell. The level of phagocytosis in a cell thus treated may be at least about 25%, at least about 50%, at least about 75%, and may increase phagocytosis 2-fold, 3-fold, 5-fold or more, relative to an unstimulated cell. In the presence of an agent that blocks the interaction of CD47 with SIRPα, the incremental increase in phagocytosis for a cell treated with an effective dose of a TLR agonist or a BTK agonist may be at least about 25%, at least about 50%, at least about 75%, and may increase phagocytosis 2-fold, 3-fold, 5-fold or more, relative to a cell treated with a TLR agonist in the absence of CD47 blockade.

For in vivo treatment, a TLR agonist or a BTK agonist can be administered in an effective dose and for a period of time sufficient to increase PrCr in the recipient, e.g. as determined by the phagocytosis of tumor cells by the phagocytic cells. The TLR agonist or a BTK agonist may be co-administered or concurrently administered with an effective dose of an agent that blocks the interaction of CD47 with SIRPα. The TLR agonist or a BTK agonist may be co-administered or concurrently administered with an agent that specifically targets a cancer cell, e.g. an antibody directed to a tumor selective target.

Phagocytic cells that have been treated in vitro with a TLR agonist or a BTK agonist can be administered to an individual for treatment of cancer, where the cells are administered systemically or locally, e.g. at a tumor site. The cells may be co-administered or concurrently administered with an effective dose of an agent that blocks the interaction of CD47 with SIRPα. The cells may be contacted with a tumor cell or tumor cell antigen in vitro prior to administration. The cells may be co-administered or concurrently administered with an agent that specifically targets a cancer cell, e.g. an antibody directed to a tumor selective target.

The phagocytic capability of a phagocyte, e.g. a macrophage, can be determined by measuring the expression of CRT on the cell surface, where an increase in CRT corresponds to an increase in phagocytic ability. In some embodiments, the expression of calreticulin on a macrophage cell surface is measured, including without limitation by contacting the cell with a CRT-specific antibody, and determining the quantity of antibody that is bound, e.g. by flow cytometry, ELISA, immunohistochemistry, and the like as known in the art. In some such embodiments the measuring step is performed after treating the cells with a TLR agonist in vitro. In some embodiments, the measuring is compared to a pre-determined level, or a control cell that is not treated with a TLR agonist. In some embodiments, cells that have a predetermined level of CRT are administered to an individual for treatment of cancer, where the cells are administered systemically or locally, e.g. at a tumor site.

In other embodiments of the invention, an inhibitor of BTK, including without limitation ibrutinib, is provided in a therapeutic dose to an individual suffering from excessive or otherwise undesirable PrCR, including without limitation an individual suffering from myelodysplastic syndrome (MDS), autoimmune hemolytic anemia (AIHA), immune thrombocytopenic purpura (ITP), etc. The dose of BTK inhibitor is sufficient to downregulate expression of CRT on phagocytic cells, e.g. decrease by least about 25%, at least about 50%, at least about 75%, and may decrease expression 2-fold, 3-fold, 5-fold or more, relative to an unstimulated cell. The level of phagocytosis in a cell thus treated may be reduced by at least about 25%, at least about 50%, at least about 75%, and may decrease phagocytosis 2-fold, 3-fold, 5-fold or more, relative to an unstimulated cell.

EXAMPLE 1

Macrophages eat cancer cells using their own calreticulin as a guide: roles of TLR and BTK Macrophage-mediated programmed cell removal (PrCR) is an important mechanism of eliminating diseased and damaged cells prior to programmed cell death. The induction of PrCR by "eat me" signals on tumor cells is countered by "don't eat me" signals such as CD47, which binds macrophage signal-regulatory protein a (SIRPa) to inhibit phagocytosis. Blockade of CD47 on tumor cells leads to phagocytosis by macrophages. Here we demonstrate that the activation of toll-like receptor (TLR) signaling pathways in macrophages synergizes with blocking CD47 on tumor cells to enhance PrCR. Bruton's tyrosine kinase (BTK) mediates TLR signaling in macrophages. Calreticulin, previously shown to be an "eat me" signal on cancer cells, is activated in macrophages for secretion and cell surface exposure by TLR and Btk, to target cancer cells for phagocytosis, even if the cancer cells do not themselves express calreticulin.

Programmed cell removal (PrCR) is a process of macrophage-mediated immunosurveillance by which target cells are recognized and phagocytosed. PrCR was previously known as a key step concurrent with programmed cell death for the clearance of apoptotic cells, but when apoptosis is blocked, PrCR of neutrophils that are living (due to enforced expression of bcl2) occurs precisely at the same time that PrCR removes dying wild-type neutrophils. Recently a role for PrCR in eliminating living tumor cells has been revealed. Several studies have indicated a crucial function of CD47 as an anti-phagocytic "don't eat me" signal dominating over PrCR. During cancer development, tumor cells upregulate CD47, which protects them from PrCR. Blockade of the interaction between CD47 on target cells and its receptor, signal-regulatory protein a (SIRPα), on macrophages elicits efficient PrCR of cancer cells, but not most normal cells in vitro and in vivo (FIG. 1A). When CD47 is blocked, cancer cells, but not normal cells, are phagocytosed because pro-phagocytic "eat me" signals such as calreticulin (CRT) are commonly expressed on many leukemias, lymphomas, and solid tumors (FIG. 1A).

Calreticulin is normally an endoplasmic reticulum (ER) protein possessing ER retention KDEL sequences, but can be released to the cell surface in many instances of cell damage by cytotoxic drugs or inflammation and is recognized by macrophage LRP1/CD91 during phagocytosis of apoptotic cells. Bruton's tyrosine kinase (Btk) is a member of the Tec nonreceptor protein tyrosine kinase family, which plays a crucial role in the regulation of the innate immune response. A defect of Btk leads to immunodeficiencies including X-linked hypo- or agammaglobulinemia, presumably due to the blockade of B cell development, and perhaps related to inefficient clearance of defective B-lineage cells as well. So far, however, little is known concerning the molecular mechanisms by which macrophages recognize and phagocytose living cancer cells. We show here that macrophages express calreticulin, and that Toll-like receptor (TLR) signaling through Btk results in its trafficking to the cell surface, where it can be used to mediate PrCR of appropriate tumor cells.

We performed phagocytosis assays by co-culturing mouse bone marrow-derived macrophages (BMDMs) and target human cancer cells to examine the efficacy of PrCR under different conditions. To induce phagocytosis, we blocked CD47 on a human colon cancer cell line (SW620) by either treating tumor cells with CD47 blocking antibodies or directly knocking it out. Phagocytosis was significantly increased by knocking out the self-protective signal CD47 (SW620$^{CD47KO}$; FIG. 5, A-B), resulting from an imbalance of "eat me" over "don't eat me" pathways (FIG. 1A). Treatment of SW620$^{WT}$ cells with anti-CD47 antibody elicited stronger phagocytosis which was reversed by Fc-receptor blockers to the same level as that of SW620$^{CD47KO}$ cells, suggesting that anti-CD47 antibody induced phagocytosis of SW620 cancer cells by both blockade of CD47-SIRPα interactions (Fc-independent) and with Fc-dependent mechanisms (FIG. 1A).

To understand the molecular mechanisms of PrCR, we performed screening experiments to identify signaling pathways that regulate phagocytic ability of macrophages. TLR signaling plays a crucial role in the innate immune response against pathogens, and TLR agonists are listed as immunotherapeutic agents with anti-cancer potential. However, the role of TLR signaling in PrCR of living cancer cells remains unexplored. Thus, we pretreated BMDMs with various TLR agonists and then assayed their phagocytotic ability against cancer cells. We found that the activation of multiple TLRs significantly enhanced phagocytosis of cancer cells (FIG. 1B). We next focused on the TLR agonists that were most effective at enhancing phagocytosis, assessing their effects on a wider range of macrophages and tumor cells. We showed that treatment of macrophages with TLR3, 4 and 7 agonists (i.e., polyinosinic-polycytidylic acid-high molecular weight (Poly (I:C) HMW), lipopolysaccharide (LPS), and imiquimod) dramatically enhanced their phagocytosis of multiple hematopoietic and solid tumor cells (FIGS. 6A-C and 7 A-D). Subsequent assessment in mice lacking T-, B- and NK cells, showed that these TLR agonists significantly improved the efficacy of CD47 blocking antibody to block tumor growth in vivo (FIG. 8, A-B).

Figure 2B:
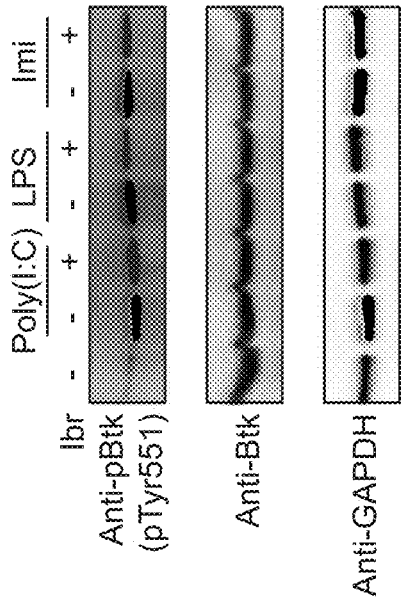
FIG. 2A-2D. Btk is the key signaling molecule regulating PrCR of cancer cells.
Figure 2D:
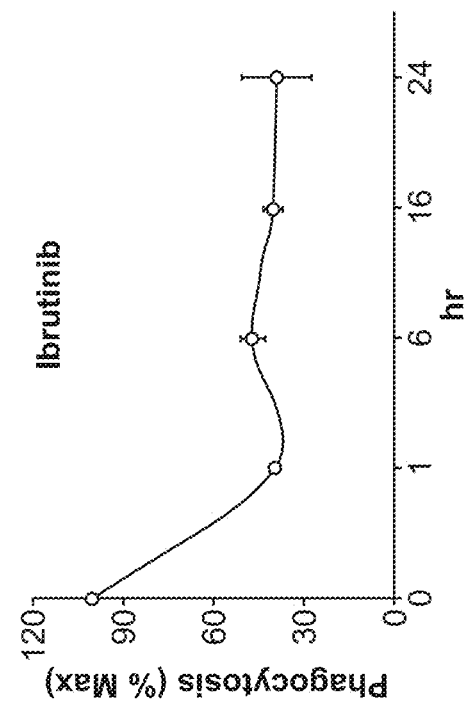
Figure 2A:
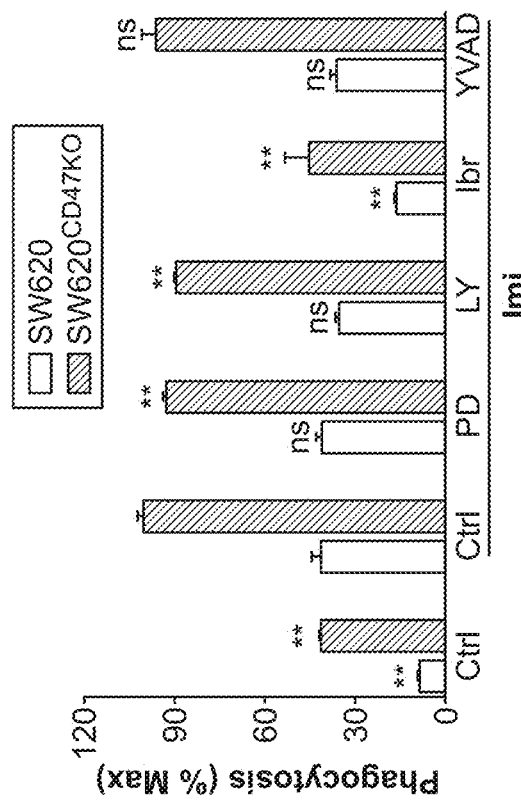
Figure 2C:
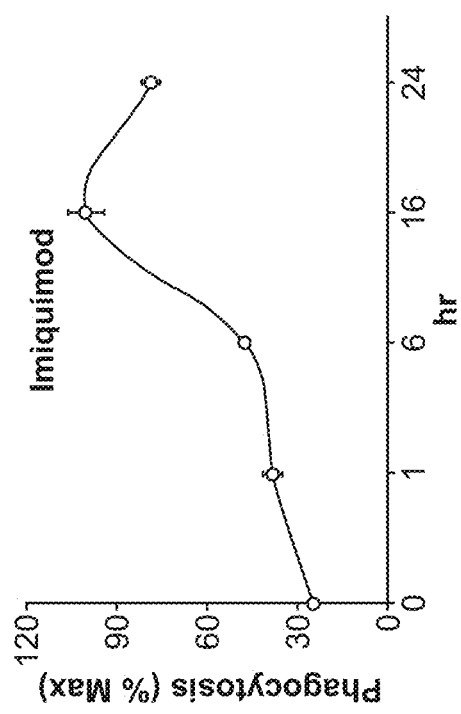

To further understand the mechanism by which the activation of TLR signaling in macrophages promoted tumor cell phagocytosis, we treated macrophages by combining TLR agonists with various inhibitors targeting key molecules that positively (MAPK, Btk) or negatively (PI3K, Caspase-1) regulate TLR signaling. Blockers of MAPK, PI3K, and Caspase1 showed no effect on phagocytosis of cancer cells. In contrast, ibrutinib—a specific blocker of Bruton's tyrosine kinase (Btk), a tyrosine kinase expressed in the hematopoietic system (FIG. 9), significantly attenuated phagocytosis induced by TLR agonists (FIG. 2A). Treatment of macrophages with Poly (I:C) HMW, LPS, or imiquimod stimulated Btk to be phosphorylated, and this effect was counteracted by ibrutinib, resulting in basal Btk phosphorylation (FIG. 2B). Notably, basal level phagocytosis of cancer cells was regulated by the Btk pathway, and ibrutinib showed an inhibitory effect on both Fc-dependent and-independent phagocytosis (FIG. 10A). In sum, Btk is a crucial effector through which TLRs mediate tumor cell phagocytosis. Interestingly, stimulation and inhibition of Btk showed differential temporal effects on phagocytosis. Maximal phagocytic ability of macrophages was achieved with 16 hr of Btk-activation (FIG. 2C); In contrast, blockade of Btk showed a prompt effect and reached the maximal inhibition within 1 hr (FIG. 2D).

Figure 10E:
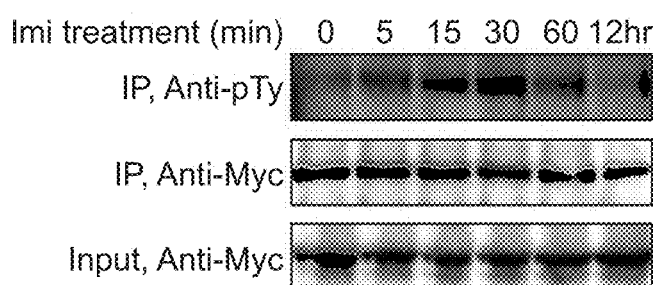

Upon activation, Btk phosphorylates transcription factors such as TFII-I and STAT5A in the nucleus and PLCγ2 at the plasma membrane. Recent studies identified CRT as a substrate phosphorylated by Btk when TLR7 was activated in the recognition of apoptotic cells. Phosphorylation of CRT by Btk in macrophages was important for CRT trafficking to the cell surface to function as a bridging molecule in the CRT/CD91/C1q complex, which initiates phagocytosis of apoptotic cells. To investigate whether CRT is the critical downstream effector of TLR-Btk pathway to mediate PrCR of tumor cells, we then examined the expression and function of CRT in macrophages. We found that CRT was expressed on the surface of macrophages, and its cell surface exposure was regulated by the activation status of Btk (FIG. 3, A-B, FIG. S6B). CRT antibody significantly inhibited phagocytosis of SW620 cells by mouse BMDMs or human peripheral blood mononuclear cells (PBMC)-derived macrophages (FIG. 3C and FIG. 10C-D), while overexpression of CRT in a mouse monocyte/macrophage cell line J774 led to enhanced phagocytosis (FIG. 3D). In addition, we confirmed phosphorylation of CRT upon Btk activation, which reached the maximal level after 30 min of imiquimod treatment of macrophages (FIG. 10E). These results suggest that CRT is an essential component regulated by the TLR-Btk pathway to mediate phagocytosis of living cancer cells.

Figure 4A:
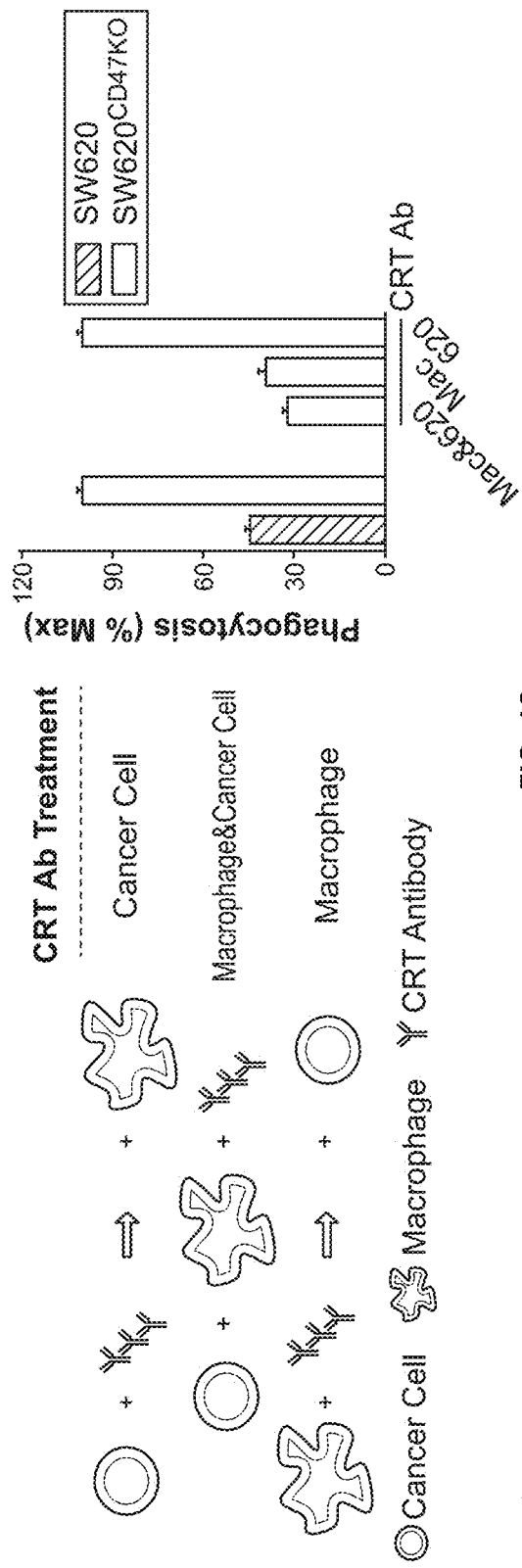
FIG. 4A-4C. CRT is a key effector on macrophages in mediating PrCR of cancer cells.
Figure 4C:
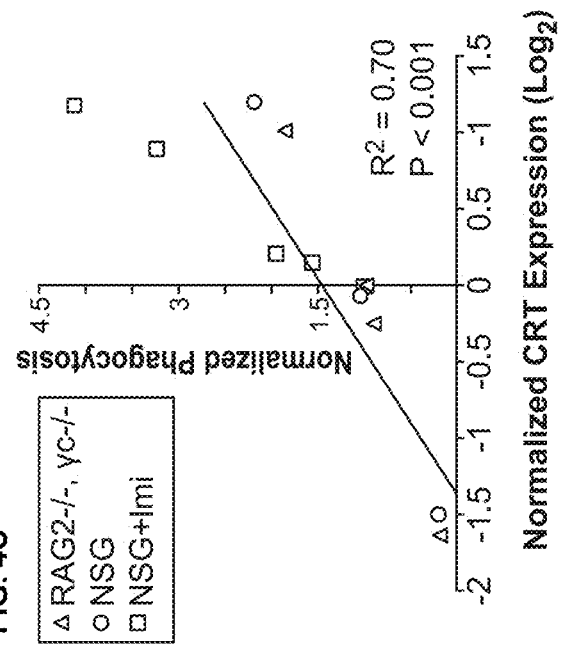
Figure 4B:
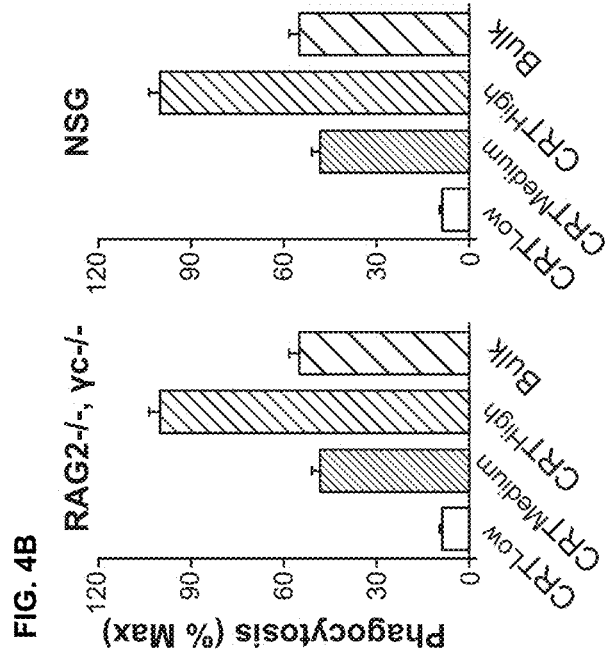
Figure 12A:
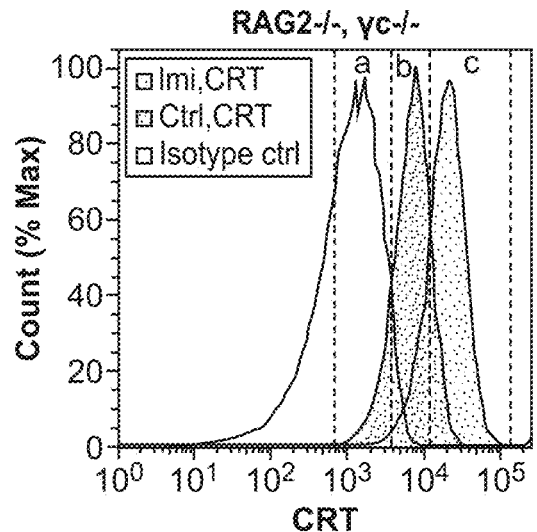
Figure 12B:
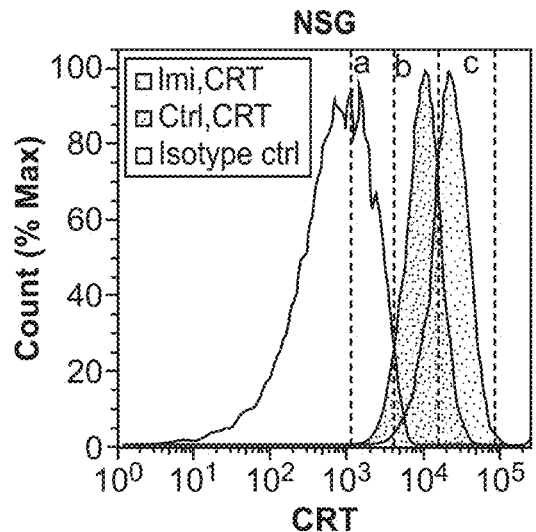
Figure 12C:
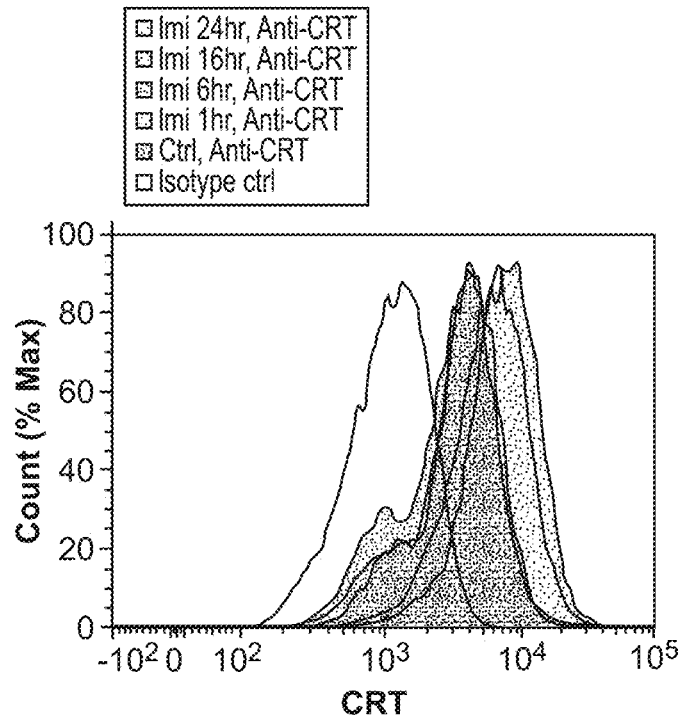
Figure 12D:
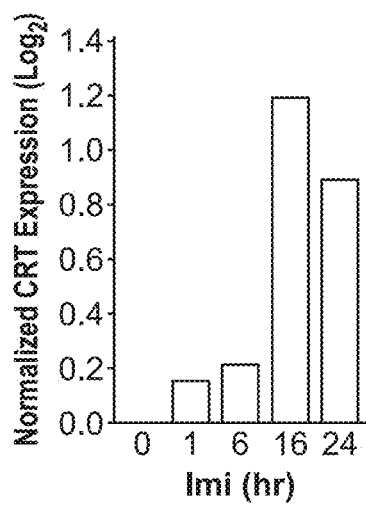
Figure 13A:
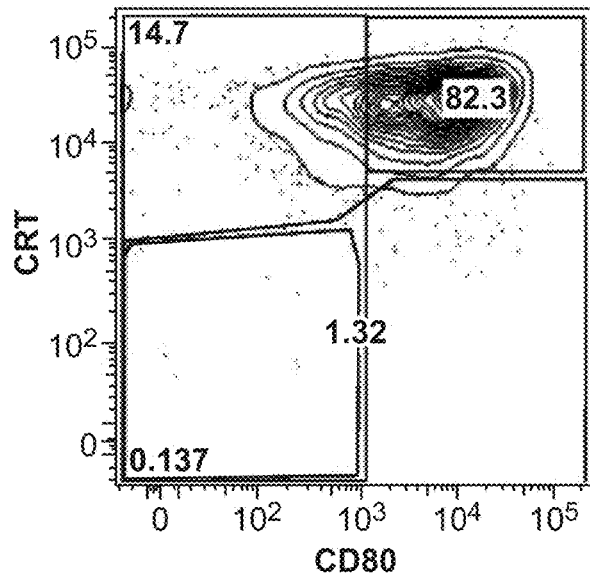
Figure 13B:
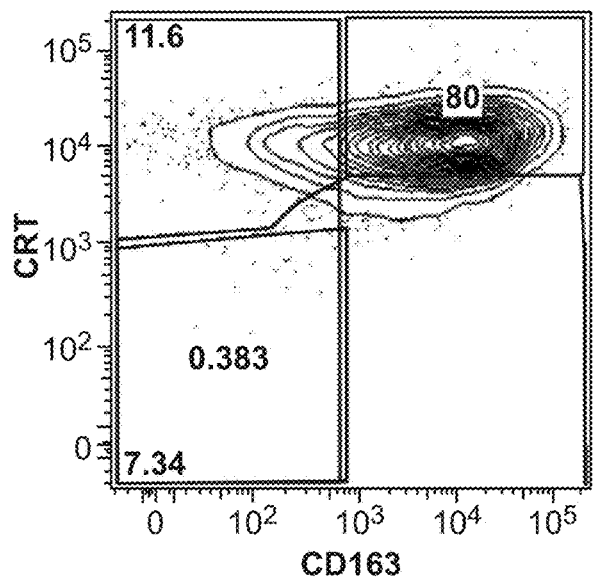
Figure 13C:
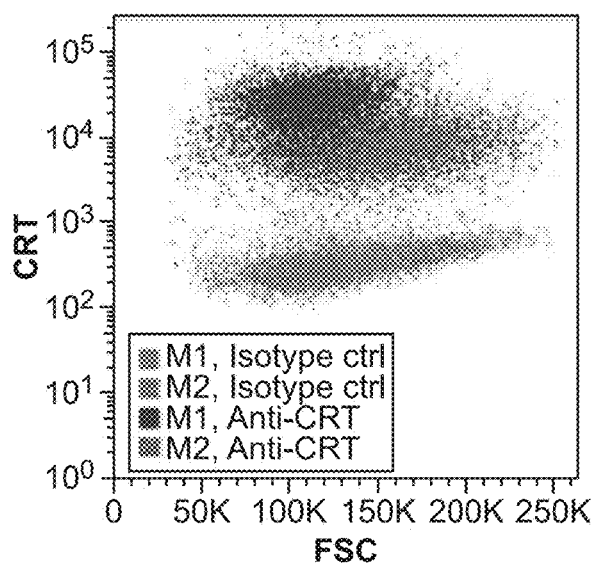
Figure 13D:
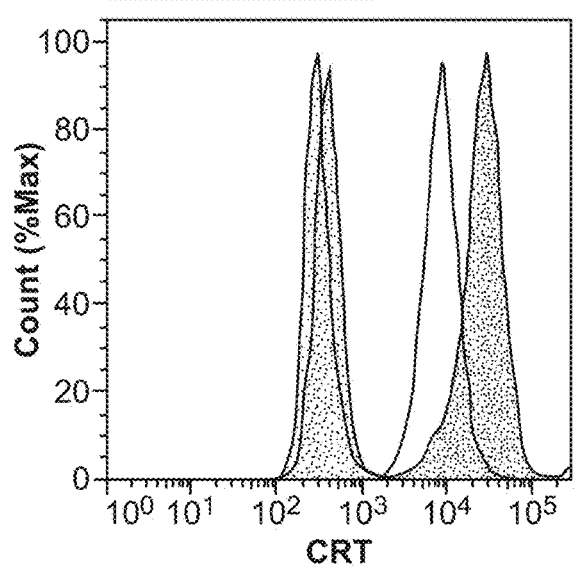

We further dissected the role of CRT in mediating PrCR of cancer cells. Previous studies demonstrated cell surface expression of CRT on apoptotic cells and multiple viable human cancer cells (FIG. 11, B-D). Thus we examined whether CRT played a critical role in mediating cancer cell phagocytosis on both macrophages and target tumor cells (FIG. 4A). Interestingly, blockade of CRT on macrophages diminished phagocytosis but blocking CRT on cancer cells showed no effect, suggesting a specific role of CRT on macrophages to mediate phagocytosis (FIG. 4A). Importantly, cell surface expression of CRT was enhanced by TLR agonists in macrophages but not target cancer cells, which lack Btk (FIG. 11, A-D), indicating distinct mechanisms regulating CRT exposure. Next, we examined macrophage sub-populations with different levels of cell surface CRT and found that macrophages with a higher surface CRT showed a stronger phagocytic ability (FIG. 4B and FIG. 12A-B). Quantitative analysis of a panel of macrophages, including sub-populations with differential surface CRT expression and macrophages at different time points after imiquimod treatment, revealed a significant correlation between CRT expression on macrophages and tumor cell phagocytosis (FIG. 4C and FIG. 12C-D). Additionally, M1 and M2 human macrophages derived from the peripheral blood both expressed CRT on the surface, and M1 subset expressed a somewhat higher level of CRT (FIG. 13). Taken together, these findings indicate that CRT is a key effector for macrophage-mediated surveillance of tumor cells and enhanced PrCR of cancer cells can be achieved by upregulating CRT on macrophages.

Recent progress in cancer immunology has highlighted the ability of cancer cells to evade immunosurveillance as one of the essential hallmarks of cancer. While lymphocytes (T, B, and NK cells) have been thought to mediate the bulk of anti-cancer immunosurveillance, we have demonstrated that blockade of CD47 on tumor cells leads to in vivo immune recognition, macrophage phagocytosis of tumor cells, and tumor elimination in mice deficient in lymphocytes, indicating that phagocytes are crucial to surveillance against cancer cells. Phagocytosis of tumor cells mediated by anti-CD47 blockade can result in cross-presentation of tumor antigens to CD8 T cells, so that CD47 blockade can result in both innate immune system macrophage surveillance and stimulation of adaptive immune system T cell cytotoxicity.

Here we show that cell surface CRT on macrophages, which is controlled by the TLR-Btk pathway in causing phosphorylation of endoplasmic reticulum CRT, its cleavage from the ER retention signals with subsequent secretion, where it is able to bind to macrophage CD91. We show that this mechanism of secretion is important for mediating PrCR of live cancer cells, in addition to the demonstration of this mechanism to remove apoptotic cells. CRT on macrophages may function in detecting target cells through trans-interaction with as yet unidentified specific receptors on target cancer cells; thus blockade of surface CRT inhibits PrCR. Moreover, CD47 mutant mice do not phagocytose self red cells or hematopoietic stem cells (HSC), but these cells are rapidly phagocytosed when transferred to wild type congenic normal or irradiated mice, even though neither cell type expresses CRT in microarrays, indicating other "eat me" signals could be used, or that CRT can decorate target cells that do not express calreticulin genes.

We show that multiple types of TLR agonists are able to stimulate macrophages and enhance PrCR of solid tumor cells, consistent with reports that TLR4 agonist LPS and IFN-γ receptors were necessary for activating macrophages to phagocytose acute myeloid leukemia cells after disrupting CD47-SIRPα interaction. It is possible from these studies that TLR signaling can synergize with anti-CD47 blockade to enhance tumor cell phagocytosis, but the potential for TLR signaling of normal cells, creating them also as targets for phagocytosis, must be tested in several systems before one can judge the clinical potential of such synergy. Further investigation of the interaction between macrophages and target cancer cells should advance our understanding of the principles of cancer cell immune evasion.

Materials and Methods

Mice. BALB/c, RAG2$^{-/-}$ γc$^{-/-}$ BALB/c and NOD.Cg-Prkdc$^{scid}$ Il2rg$^{tm1Wjl}$/SzJ (NSG) mice were bred in a pathogen-free facility in the Institute for Stem Cell Biology and Regenerative Medicine at Stanford University. All animal procedures were approved by the Administrative Panel on Laboratory Animal Care at Stanford University.

Cell culture. Human cancer derived cell lines SW620 (colon cancer), HL60 (leukemia), Raji (lymphoma), MDA-MB-231 (breast cancer), PC3 (prostate cancer) and murine macrophage/monocyte cell line J774 were obtained from ATCC and routinely cultured in DMEM medium supplemented with 10% fetal bovine serum (SW620, MDA-MB-231, J774), IMDM medium supplemented with 20% fetal bovine serum (HL60), F-12K medium supplemented with 10% fetal bovine serum (PC-3), or RPMI-1640 medium supplemented with 10% fetal bovine serum (Raji). Tumor cells were transduced with lenti viruses which were generated with a pCDH-CMV-MCS-EF1 lenti viral vector expressing a luciferase-eGFP fusion protein and sorted by flow cytometry with BD FACSAria II cell sorters for GFP+ cells, as described previously.

CD47 knockout with TALEN. TALENs were designed and assembled as described. The genomic locus of human CD47 (NC_000003.12) was scanned for putative TALEN binding pairs. Exon 2 was ultimately selected for targeting and the TALEN pairs SEQ ID NO: 2 TGTCGTCATTC-CATGCTTTG and SEQ ID NO: 3 TATACTTCAGTAGTGTTTTG were respectively cloned into the pTALEN backbone. SW620 cells were transfected with the CD47-TALEN constructs using lipofectamine 2000. Three days after transfection, cells were stained with anti-CD47 or Isotype antibodies. CD47-cells were sorted by flow cytometry with BD FACSAria II cell sorters.

Flow cytometry Analysis. Flow cytometry analyses were performed using a BD LSRFortessa. For staining, $2.5 \times 10^6$-$10^6$ cells were incubated with indicated antibodies (1:50-1:200) in FACS buffer (PBS with 2% fetal bovine serum) on ice for 30 minutes. Cells were then washed with FACS buffer and subjected to FACS analyses. For staining of macrophages, cells were first treated with Fc receptor blockers or a high concentration of isotype IgG control (5-10 times of indicated antibodies) to block non-specific binding of antibodies caused by the interaction of Fc domain and Fc receptors on macrophages.

Preparation of macrophages. Human peripheral blood-derived macrophages were generated as previously described. Monocytes were enriched from human peripheral blood and differentiated to macrophages by culture in IMDM supplanted with 10% human serum for 7-10 days. To generate M1 human macrophages, monocytes were treated with recombinant human GM-CSF (5 ng/mL) in RPMI 1640 medium supplemented with 5% FBS and 1% glutamax over all 7 days. M1 polarization was achieved by further treatment on day 5 by IFN-γ (20 ng/mL) stimulation for 1 hr, followed by LPS (100 ng/mL) treatment on days 6-7. To generate M2 human macrophages, monocytes were treated with recombinant human M-CSF (25 ng/mL) in RPMI 1640 medium supplemented with 5% FBS and 1% glutamax over all 7 days. M2-polarization was achieved by further treatment on day 5 and 6 with IL-4 (20 ng/mL) and IL-13 (20 ng/mL). Differentiation of M1- and M2 macrophages were evaluated by the expression of specific surface makers CD80 (M1) and CD163 (M2).

Anti-CD47 (BD Biosciences), anti-calreticulin (Enzo Life Sciences, Abcam and MBL International), anti-F4/80 antibodies (Biolegend), anti-CD31 antibody (BD Biosciences), anti-Gr-1 antibody (Biolegend) were used for FACS analyses. Antibodies were Phycoerythrin (PE)-, PE cy-7-, APC- or Brilliant Violet 421 (BV421)-conjugated, or fluorophore-conjugated secondary antibodies were used. Sytox blue was used to exclude dead cells.

Phagocytosis assay. FACS-based phagocytosis assays were performed to evaluate phagocytic abilities of macrophages. Macrophages were harvested after 6-8 days of differentiation and divided into FACS tubes or low-attachment 96-well plates, with $1-5 \times 10^4$ cells per well/tube. Target cells were added and mixed with macrophages, and incubated at 37° C. for 2 hrs with indicated conditions (antibody/drug treatment). For CD47 blockade, anti-CD47 (B6H12, BD Biosciences) or humanized anti-CD47 (Hu5F9-G4; provided by the CD47 disease team at Stanford University) antibodies were used. Cells were then incubated with PE cy7-conjugated anti-mouse F4/80 antibody to stain macrophages. After incubation, cells were washed with FACS buffer and resuspended with FACS buffer containing sytox blue to distinguish dead cells. Phagocytic index was examined by FACS analyses, and macrophages that phagocytosed target cells were F4/80+ and GFP+. Phagocytic index was calculated with the number of F4/80+GFP+ cells/divided by the number of F4/80+ cells. In each experiment, phagocytic indexes were normalized to the maximal indexes.

Alternatively, macrophages and target cells were mixed and cocultured in 24 well plates for 16-24 hrs with indicated conditions. Cells were collected from the plates by TrypLE and incubated with PE cy7-conjugated anti-mouse F4/80 antibody to stain for macrophages. After incubation, cells were washed with FACS buffer and resuspended with FACS buffer containing sytox blue and non-colored standard cells (293T cells were used as standard cells). Cells were then subjected to FACS analyses. Remaining target cells were normalized to standard cells (numbers of standard cells were known and equal in each sample) to evaluate the percentage of cells phagocytosed by macrophages during the incubation.

For the experiments investigating phagocytic ability of macrophages with differential cell surface expression of CRT, cells were stained with anti-F4/80 antibody, as well as anti-calreticulin antibody or isotype control conjugated to the same color after phagocytosis assay. F4/80+ cells (macrophages) were gated, among which $CRT^{High}$, $CRT^{Medium}$ or $CRT^{Low}$ cells were analyzed separately for phagocytic indexes.

Overexpression of CRT. Replication-incompetent lentivirus was used to overexpress calreticulin in J774 cells. CRT cDNA was cloned into pCDH-MCS-IRS-Puro lenti viral vector, with a myc tag after the signal peptide. The lentiviral vector expressing myc-tagged CRT was transiently transfected to 293T cells with psPAX2 and pMD2.G at a ratio of (4:3:1). 48 hrs after transfection, the supernatant was collected and added to J774 cells. Cells were treated with puromycin (2 μg/ml) for 48 hrs and selected cells were used for phagocytosis assays. CRT overexpression was confirmed by western blot with anti-myc antibody.

Cell surface biotinylation. Mouse bone marrow derived macrophages were seeded on day 6, and treated with imiquimod or ibrutinib for 16 hrs before biotinylation assay. Cells were incubated with NHS-SS-Biotin (0.5 mg/ml) for 1 hr in PBS (pH8.0), and then rinsed with quench buffer (20 mM Tris-HCl, 120 mM NaCl, pH7.4), 100 mM Glycine in PBS, and PBS. Cells were lysed in lysis buffer (20 mM Tris-HCl, pH7.4, 150 mM NaCl, 2 mM EDTA, supplemented with 1% Triton X-100, protease inhibitor cocktail and phosphatase inhibitor cocktail). Cell lysate was incubated with neutravidin agarose resin for 4 hr at 4° C., and the resin was washed using lysis buffer. Biotin-labeled proteins were eluted with lysis buffer containing 2% SDS and 100 mM DTT, and subjected to SDS-PAGE and immunoblotting. Intracellular protein GAPDH was used as a negative control to confirm that only cell surface proteins were labeled by NHS-SS-Biotin.

Immunoprecipitation. Calreticulin was immunoprecipitated from J774 cells expressing myc-CRT. J774 cells were plated 12 hrs before immunoprecipitation. Cells were treated with imiquimod (1 ug/ml) at indicated time points, and washed with pre-chilled PBS containing phosphatase inhibitors on ice. Cells were then lysed in lysis buffer (20 mM Tris-HCl, pH7.4, 150 mM NaCl, 2 mM EDTA, supplemented with 1% Triton X-100, protease inhibitor cocktail and phosphatase inhibitor cocktail). Cell lysate was incubated for 1 hr with GammaBind Plus Sepharose for pre-clearance and 4 hr with anti-myc antibodies at 4° C. GammaBind sepharose was added to cell lysate and incubated for 1 hr at 4° C. Beads were washed with lysis buffer. Proteins were eluted with lysis buffer containing 2% SDS and 100 mM DTT, and subjected to SDS-PAGE and immunoblotting. To detect phosphorylated CRT, the blot was incubated with biotin-labeled pT66 anti-p-Tyrosine antibody and HRP-conjugated streptavidin.

Tumor engraftment and treatment. PC3 cells (human prostate cancer) were suspended in F-12K medium with 25% matrix matrigel, and injected subcutaneously on the back of 6-10 week NSG mice. Mice were treated with PBS or Hu5F9-G4 antibody by intraperitoneal injection 2 weeks after engraftment, and PBS or TLR agonists (20 μg of Poly (I:C) HMW and 20 μg of LPS) by intratumoral injection 7 weeks after engraftment when tumors reached 100 mm$^3$.

Bioluminescent imaging was performed to monitor tumor growth, as described before. Briefly, D-Luciferin (firefly) potassium salt was dissolved in PBS to a final concentration of 16.6 mg/ml. Mice were injected intraperitoneally with luciferin solution (0.139 g luciferin/kg body weight), and imaged and analyzed with Living Image 4.0 software.

Tumor dissociation and FACS analyses. Tumor specimens were collected from the mice, minced to pieces smaller than 1 mm in diameter and dissociated in medium 199 with TM enzymes and DNAase at 37° C. until single-cell suspension was achieved. The cells were treated with ACK lysing buffer for lysis of red blood cells, washed twice with HBSS, filtered through 70 μm cell strainer and subjected to flow cytometry analyses. The cells were stained with anti-CD31 antibody, anti-Gr-1 antibody and sytox blue to exclude endothelial cells, neutrophils and dead cells, and with anti-F4/80 antibody for macrophages.

What is claimed is:

1. A method of enhancing programmed cell removal of living cancer cells, the method comprising:
   contacting a population of phagocytic cells with a btk activating TLR agonist in a dose effective to increase expression of calreticulin on the phagocytic cell surface; and with an anti-CD47 antibody that blocks binding of CD47 to SIRPα and comprises an Fc region in a dose effective to increase programmed cell removal of the living cancer cells;
   wherein programmed cell removal of cancer cells by the phagocytic cells is enhanced.

2. The method of claim 1, wherein the contacting is performed in vivo.

3. The method of claim 1, wherein the contacting is performed in vitro.

4. The method of claim 1, wherein the phagocytic cells are macrophages.

5. The method of claim 1, wherein the antibody is a humanized IgG4 antibody.

6. The method of claim 1, wherein the btk activating TLR agonist is an agonist of TLR7, TLR8 or TLR9.

7. The method of claim 6, wherein expression of calreticulin on the phagocytic cell surface is measured prior to the introducing step.

8. The method of claim 6, wherein the agonist of TLR8 is a viral ssRNA mimic.

9. The method of claim 6, wherein the TLR7 agonist is a synthetic imidazoquinoline.

10. The method of claim 6, wherein the TLR9 agonist is CpG containing oligonucleotide.

* * * * *

SEQUENCE LISTING

<160> NUMBER OF SEQ ID NOS: 3

<210> SEQ ID NO 1
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 1

Lys Leu Gly Phe Phe Lys Arg
1               5

<210> SEQ ID NO 2
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 2
tgtcgtcatt ccatgctttg                                               20

<210> SEQ ID NO 3
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 3
tatacttcag tagtgttttg                                               20